(12) United States Patent
Edgar

(10) Patent No.: US 11,090,474 B2
(45) Date of Patent: Aug. 17, 2021

(54) DEVICE AND METHOD FOR APPLICATION OF TOPICAL COMPOSITIONS GUIDED BY PROJECTED FIDUCIALS

(71) Applicant: JOHNSON & JOHNSON CONSUMER INC., Skillman, NJ (US)

(72) Inventor: Albert Durr Edgar, Austin, TX (US)

(73) Assignee: JOHNSON & JOHNSON CONSUMER INC., Skillman, NJ (US)

( * ) Notice: Subject to any disclaimer, the term of this patent is extended or adjusted under 35 U.S.C. 154(b) by 0 days.

(21) Appl. No.: 16/726,587

(22) Filed: Dec. 24, 2019

(65) Prior Publication Data

US 2020/0206487 A1  Jul. 2, 2020

Related U.S. Application Data

(60) Provisional application No. 62/785,482, filed on Dec. 27, 2018.

(51) Int. Cl.
| | |
|---|---|
| *A61M 35/00* | (2006.01) |
| *G06T 7/11* | (2017.01) |
| *G06T 7/12* | (2017.01) |
| *G06T 7/00* | (2017.01) |

(52) U.S. Cl.
CPC ......... *A61M 35/003* (2013.01); *G06T 7/0012* (2013.01); *G06T 7/11* (2017.01); *G06T 2207/30088* (2013.01); *G06T 2207/30204* (2013.01)

(58) Field of Classification Search
USPC ....................................................... 348/128
See application file for complete search history.

(56) References Cited

U.S. PATENT DOCUMENTS

| | | |
|---|---|---|
| 8,007,062 B2 | 8/2011 | Edgar et al. |
| 8,027,505 B2 | 9/2011 | Edgar et al. |
| 8,942,775 B2 | 1/2015 | Edgar et al. |
| 9,020,184 B2 | 4/2015 | Edgar |
| 9,247,802 B2 | 2/2016 | Edgar et al. |
| 9,449,382 B2 | 9/2016 | Edgar et al. |
| 9,462,872 B2 | 10/2016 | Edgar |

(Continued)

FOREIGN PATENT DOCUMENTS

| | | |
|---|---|---|
| WO | 2010/145669 | 12/2010 |
| WO | 2015/191824 | 12/2015 |

*Primary Examiner* — Patricia I Young
(74) *Attorney, Agent, or Firm* — Fay Kaplun & Marcin, LLP

(57) ABSTRACT

A device and a method are for application of a composition to a treatment surface (e.g., skin). The device may include an optical emitter projecting fiducials to skin; a detector obtaining image data corresponding to an image of an area of skin marked with the fiducials; an applicator applying the composition to a location within the skin area; and a processing arrangement. The processing arrangement is receiving the image data, analyzing the image data to determine a morphology of the skin area based on the fiducials captured within the image, identifying, based on the morphology, a region within the image corresponding to the location aimed by the applicator arrangement, analyzing the image data to determine whether the identified region corresponds to a skin artifact, and directing the applicator arrangement to selectively apply the composition to the location when the skin artifact is detected from the identified region.

24 Claims, 7 Drawing Sheets

(56) References Cited

U.S. PATENT DOCUMENTS

| | | |
|---|---|---|
| 10,092,082 B2 | 10/2018 | Edgar et al. |
| 10,486,174 B2 | 11/2019 | Edgar et al. |
| 10,553,006 B2 | 2/2020 | Iglehart et al. |
| 2009/0025747 A1* | 1/2009 | Edgar .................. B05B 5/1691 132/320 |
| 2019/0080451 A1* | 3/2019 | Iglehart ............... A61C 19/063 |

* cited by examiner

DEVICE AND METHOD FOR APPLICATION OF TOPICAL COMPOSITIONS GUIDED BY PROJECTED FIDUCIALS

PRIORITY CLAIM

This application claims priority to U.S. Provisional Application Ser. No. 62/785,482 filed Dec. 27, 2018, the entire contents of which is hereby incorporated by reference herein.

FIELD OF INVENTION present invention relates to devices and methods for applying a composition to a treatment surface, such as a keratinous surface (e.g., the skin, hair or nails) or enamel (e.g., teeth). More specifically, the invention relates to devices and methods for selectively applying a topical composition as guided by imaging of the skin to identify areas for enhancing the aesthetic appearance of skin.

BACKGROUND

Traditional topical composition application often requires manual application that does not discriminate between area of the skin whose appearance is in need of modification and those that do not require any modification. For example, people seeking to cover or alter the appearance of features on the skin (e.g., acne, scars, age spots, etc.) typically apply a layer of a foundational base of make-up across the entire surface of the skin to create a uniform appearance that may result in an unnatural or caked-on appearance. Applying cosmetics indiscriminately over large areas of skin also wastes material as the cosmetic is also applied to portions of the skin that may need little or no modification. However, it is also difficult to manually apply cosmetics to only those portions of skin in need of modification with sufficient precision and control without creating an unnatural or splotchy appearance. In addition, manual application of a continuous layer of a topical composition may impart a film over large portions of skin, which may cause a displeasing, less natural feel for the skin. Such a film over large portions of skin may also decrease breathability of the skin and increase exposure of the skin to the topical material, which can increase the surface area of skin exposed to potential allergens and therefore, increase the risk that a user may have undesired or allergic reactions to the topical material.

SUMMARY OF THE INVENTION

One exemplary embodiment of the present invention is directed to a method for application of a composition to a treatment surface of a user, for example, the skin of a user's face. The method comprises projecting, by an optical emitter, a plurality of fiducials to the treatment surface and obtaining, by a detector arrangement, image data corresponding to an image of an area of the treatment surface marked with the fiducials. The method also comprises analyzing, by a processing arrangement, the image data to determine a morphology of the area of the treatment surface based on the fiducials captured within the image, and identifying, by the processing arrangement, a region within the image corresponding to a location within the area of the treatment surface aimed for application of the composition by an applicator arrangement. The region is identified based on the morphology of the area of the treatment surface. The method further comprises analyzing, by the processing arrangement, the image data to determine whether the identified region within the image corresponds to an artifact, and selectively applying, by an applicator arrangement, the composition to the location within the area of the treatment surface when the artifact is detected from the identified region.

A handheld device for applying a composition to a treatment surface is also described. The device comprises an optical emitter configured to project a plurality of fiducials to the treatment surface, and a detector arrangement configured to obtain image data corresponding to an image of an area of the treatment surface marked with the fiducials. The device also comprises an applicator arrangement configured to apply the composition to a location within the area of the treatment surface. The device further comprises a processing arrangement configured to receive the image data from the detector arrangement, analyze the image data to deter mine a morphology of the area of the treatment surface based on the fiducials captured within the image, identify a region within the image corresponding to the location the applicator arrangement is configured to apply the composition, analyze the image data to determine whether the identified region corresponds to an artifact, and direct the applicator arrangement to selectively apply the composition to the location when the artifact is detected from the identified region. The region is identified based on the morphology of the area of the treatment surface.

These and other aspects of the invention will become apparent to those skilled in the art after a reading of the following detailed description of the invention, including the figures and appended claims.

DETAILED DESCRIPTION

Figure 1:
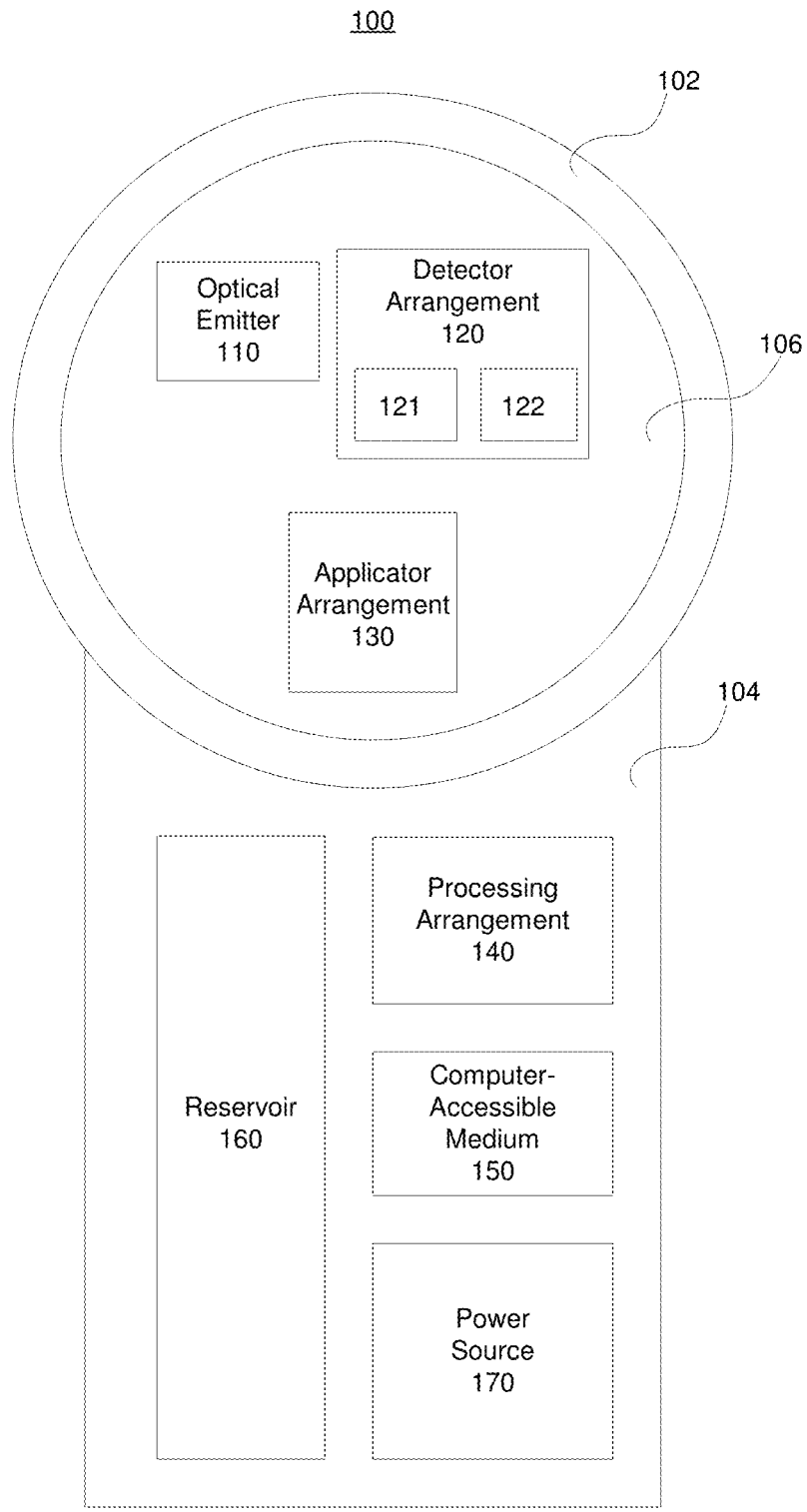
FIG. 1 shows a block diagram of an exemplary device for applying a composition to the skin of a user, according to an exemplary embodiment of the present application.

The term "frexel" as used herein refers to a small pixel-like region of skin, which corresponds to a single large pixel or a small number of pixels in a digitally obtained image. For example, a frexel may correspond to a skin area having an average diameter from about 1/15 to about 1/5 inch.

The term "middle spatial frequencies" as used herein is explained further below. For example, image data corresponding to an image of the skin can capture light reflectances extending over a range of spatial frequencies, which measures the level of detail present in an image over a distance across the skin observed by a detector (e.g., a camera) that generates the image data. Spatial frequency may be measured by the number of periodic features, e.g., described as a periodic sine-wave pattern corresponding to cycles of alternating dark and light striped patterns, within an image over a distance across the skin observed by the detector. The spatial frequency of an image may be calibrated and/or normalized based on a distance from which the skin is imaged by the detector. It is noted that spatial frequency, as used herein, does not measure a wavelength or color of light, but instead refers to a spatial wavelength of the structure of the details of the skin captured by the detector in the image. Data corresponding to an image in a spatial domain (e.g., in the form of pixels or frexel) can be processed by a computer processor using a Fourier transform function to obtain data for the image in the spatial frequency domain. This spatial frequency domain relates to an optical resolution of the image captured, which is distinct from a wavelength or color of light. As would be understood by those skilled in the art, the spatial frequency components of the image may generally be separated into three different categories, including (1) high spatial frequencies, (2) middle spatial frequencies, and (3) low spatial frequencies, using any suitable methods for image analysis, e.g., Fourier transform, filtering, etc. As would be understood by those skilled in the art, spatial frequency components having high spatial frequencies correspond to light reflectance in the image that contribute to the appearance of sharp edges and small details within the image. For example, for an image of skin, the spatial frequency components having high spatial frequencies correspond to features that appear to be small, natural variations in the skin, such as those derived from the genetic code of the person, e.g., pores, hair, follicles, cells, iris of the eye, etc. Low spatial frequencies correspond to light reflectances in the image that contribute to the broad visual appearance such as, for example, the color of larger features such as, for example, the nose, cheeks, etc. The remaining spatial frequency components between the low and spectral frequencies are referred to as the middle spatial frequencies.

The range of middle spatial frequencies may be determined relative to the image captured. For example, the range of middle spatial frequencies for an area of facial skin may be different from the range of middle spatial frequencies for an area of the skin on a leg. The range of middle spatial frequencies may also depend on the underlying skin tone of the skin imaged. In one example, the middle spatial frequencies for human skin can range from about 0.03 cycles/mm to about 1.5 cycles/mm, or more specifically from about 0.05 cycles/mm to about 1.0 cycles/mm and, even more specifically, from about 0.07 cycles/mm to about 0.5 cycles/mm.

The term "gobo" as used herein refers to a stencil or template having any shape or pattern that is disposed between a light source and a surface to which the light source projects. Light from the light source passes through the gobo to project a desired pattern of light. The projected pattern of light may correspond to the pattern of the gobo.

The present application provides a device and method for selectively applying a composition to a treatment surface. It is contemplated that the composition may be applied to any suitable treatment surface, such as, an interface between a biological surface and the external environment (e.g., air), in particular, a topical surface. Suitable biological surfaces may include keratinous surfaces (such as, but not limited to, surfaces of the skin, hair, and/or nails), and enameled surfaces (e.g., a surface of a tooth). Preferably, the treatment surface is that of a mammal or a human. Although exemplary embodiments are discussed herein relating to the skin, it is contemplated that the device and method of the present application may be used to selectively apply any suitable composition, in particular, a topical composition to a treatment surface. More particularly, the present application provides a device and method for selectively applying a topical composition to the skin (e.g., of a mammalian or human face) to address skin artifacts (e.g., scars, wrinkles, blemishes, freckles, sun damage, age spots etc.) whose appearance the user wishes to minimize or eliminate to improve an over-all aesthetic appearance of the skin. The device of the present application analyzes an image of an area of skin to identify locations to which the composition should be applied, e.g., locations at which skin artifact are detected, to alter the visual appearance of the skin. More specifically, the device and method of the present application utilizes projected optical fiducial(s) to adjustably align regions within an image captured by the detector with aimed locations of the applicator to provide a more precise and/or accurate application of the composition at desired locations on the skin. For example, the device and method of the present application may obtain image data corresponding to an image of the skin marked with projected optical fiducial(s), and analyze the image data to align regions within the image to locations aimed by an applicator and to direct the applicator to selectively deposit the composition at desired locations on the skin, for example, at those locations where a skin artifact is detected based on an analysis of a corresponding region in the image. In particular, the device and method of the present application may be used to apply a composition to the skin of the face. The composition may be a cosmetic composition and/or a skin treatment composition for improving the appearance and/or health of the skin.

FIG. 1 shows a block diagram of an exemplary device 100 for applying a topical composition to the skin. The device 100 of this embodiment is sized and shaped to be a handheld device designed to be held within a palm of a user's hand. The device 100 according to this embodiment comprises a head portion 102 and a handle portion 104. The handle portion 104 of the device 100 has an elongated shape defining a cavity for housing components therein. In some embodiments, the handle portion 104 is sized and shaped to be held within the palm of the user's hand. In other embodiments, the handle portion 104 is sized and shaped to be held by the finger tips of the user's hand.

The head portion 102 of the device 100 according to this embodiment comprises an optical emitter 110 projecting at least one fiducial to the skin, and a detector arrangement 120 obtaining image data corresponding to an image of an area of skin on which the fiducial(s) is projected. The head portion 102 of this embodiment also comprises an applicator arrangement 130 selectively applying the composition to portions of the skin as directed by a processing arrangement 140 based on image data from the detector arrangement 120. In this arrangement, the optical emitter 110 and the detector arrangement 120 are fixedly mounted relative to the applicator arrangement 130 so that the image data captured by the detector arrangement 120 can be analyzed by a processing arrangement 140 to match a location in an image to a location on the skin aimed by the applicator arrangement 130. In some embodiments, the optical emitter 110, the detector arrangement 120, and the applicator arrangement are part of an inset portion 106 of the head portion 102 such that when the head portion 102 is placed over an area of skin to be treated, the inset portion 106 is not in contact with the skin.

The optical emitter 110 comprises any suitable fiducial light source for delivering focused beam(s) of light (e.g., visible light) to project at least one fiducial onto the skin. For example, the optical emitter 110 comprises a light emitting diode (LED), particularly, a focused LED used to generate the fiducials as will be described in more detail below. The focused LED in this embodiment comprises an LED light emitter and an emissive die having a small aperture focusing light from the emitter in sharp light beams for projecting optical fiducials to the skin. Alternatively, the optical emitter 110 may comprise laser projecting fiducials onto the skin. For example, the optical emitter 110 may comprise a 650 nm Class 1 red laser or a blue (e.g., 465 nm) LED.

More particularly, the optical emitter 110 projects a plurality of fiducials onto the skin. For example, the optical emitter 110 may comprises a light source and a template (e.g., a gobo or a holographic plate) through which light from the light source passes to project fiducials onto the skin. In one example, the optical emitter 110 may provide a light source emitting light that is passed through a gobo to project fiducials onto the skin by shadowing select regions of the skin according to the patterns of the gobo, where solid regions of the gobo project shadows and cut-out regions of the gobo allow light to pass therethrough to project optical fiducial marks onto the skin. The template may be stenciled with any suitable pattern(s) for generating fiducials for determining the morphology of the imaged area of skin and/or mapping locations on the skin aimed for application of a cosmetic composition by the applicator arrangement 130 to corresponding regions (e.g., one or more pixels) within an image captured by the detector arrangement 120. For example, the template may be stenciled with a plurality of pinholes or alternatively, with a checkerboard pattern, as described further below in Example IV. Alternatively, in embodiments where the fiducial light source emits a laser light, a plurality of fiducials may be projected onto the skin via a holographic plate. The plurality of fiducials may be a plurality of point fiducials (which may be arranged in an array or in any other suitable configuration) or may be in the form of a desired pattern (e.g., a checkerboard pattern). In one example, the holographic plate comprises a diffraction grating for diffracting a single laser light source passing therethrough to project a plurality of point fiducials. In another example, the holographic plate may be a phased holographic plate having a plurality of different surface features for diffracting and/or phase varying the laser light source to project a desired pattern. It is noted that the holographic plate allows substantially all of the laser light source to pass therethrough, and therefore, provides an efficient use of the fiducial laser light source for projecting a plurality of fiducials onto the skin.

Preferably, at least 3 fiducials are projected to different locations within an imaged area of skin to provide a desired number of fiducial points within an image of the area to determine morphology of the skin with a desired degree of accuracy. The morphology of the skin may include, for example, curvature and/or tilt of the skin but may generally be considered a determination of three-dimensional shape of all or a portion of a surface of the imaged portion of skin relative to a plane of the image to understand where drops emitted from the applicator arrangement 130 will land on the skin as described in more detail below. In certain embodiments, the optical emitter 110 may project 25 or more fiducials to the imaged area of skin.

In one embodiment, the detector arrangement 120 comprises at least one light source 121 for delivering light (e.g., visible light) to an area of skin on which fiducials are projected from the optical emitter 110, and a sensor 122 detecting light, including the projected fiducials, reflected from the area of the skin. The light source 121 may comprise any suitable light emitting device for illuminating the area of skin, for example, one or more LEDs. The light source 121 may also be selected and arranged to provide an amount of illumination over the area of skin sufficient to detect and/or measure reflectance of light by the skin. Preferably, the light source(s) 121, collectively, provide a substantially uniform distribution of light over the area of skin being imaged. The sensor 122 may comprise any suitable components for detecting reflectance of light from the skin. For example, the sensor 122 may be sensitive to an amount of reflected light in one or more wavelengths. Suitable sensors 122 may include, for example, photographic or video cameras (which may include different types of camera lenses), photodiodes and/or phototransistors as would be understood by those skilled in the art.

Preferably, the light source(s) 121 of the detector arrangement 120 have a different wavelength from the fiducial light source of the optical emitter 110 such that the projected fiducials are readily distinguishable from the remainder of the image obtained by the detector arrangement. For example, the fiducial light source of the optical emitter 110 may emit red or blue light, while the light source 121 of the detector arrangement 120 emits green light. In this exemplary embodiment, the sensor 122 of the detector arrangement 120 may also comprise an RGB camera which can detect light in red, green and blue channels of the camera. Fiducials projected in red or blue light will then only be sensed by the red or blue channel, respectively, of the RGB camera, which is easily distinguishable from illumination provided by a green light source 121 of the detector arrangement 120 that will be detected in the green channel of the RBG camera. In another embodiment, the light source 121 may project a blue light and the fiducials may be in a red light, which are also easily distinguishable using the RGB camera described above.

Alternatively, the light source(s) 121 of the detector arrangement 120 may be temporally separated from the fiducial light source such that the detector arrangement 120 captures image data corresponding to a pair of images for each area of skin: (1) a first image of the area of skin illuminated by the light source 121 of the detector arrangement 120 without the projected fiducials, and (2) a second image of the same area of skin with the projected fiducials, but without illumination by the light source 121 of the detector arrangement 120, in no particular order. The first image is then analyzed by a processing arrangement 140 to match a location within the imaged area of skin aimed by an applicator arrangement 130 to a corresponding region within the first image. The same corresponding region within the second image can be analyzed by the processing arrangement 140 to determine whether the composition should be applied to the location on the skin.

The detector arrangement 120, including the light source 121 and sensor 122, is operably connected to a processing arrangement 140 to execute instructions stored on a computer-accessible medium 150. The processing arrangement 140 in this embodiment controls the light source 121 and receives and analyzes imaging data received from the sensor 122. The processing arrangement 140 can also be operably connected to the optical emitter 110 to control the optical emitter 110 so that the sensor 122 can capture images that are with or without the projected fiducials, as determined by the processing arrangement 140. Image data captured with and without projected fiducials may be used in combination to reduce distortions to the fiducials caused by variations in the color and texture of the skin, as explained further below. It is contemplated that the processing arrangement 140 and the computer-accessible medium 150 may be positioned anywhere within or external to the device 100. In one embodiment, as shown in FIG. 1, the processing arrangement 140 and the computer-accessible medium 150 are located within the handle portion 104. The processing arrangement 140 in this embodiment also controls the applicator arrangement 130 to selectively apply the composition to desired frexels. The processing arrangement 140 may be, e.g., entirely or a part of, or include, but is not limited to, a computer/processor that can include, e.g., one or more microprocessors, and use instructions stored on a computer-accessible medium 150 (e.g., memory storage device). The computer-accessible medium 150 may, for example, be a non-transitory computer-accessible medium containing executable instructions therein. A storage arrangement may be provided separately from the computer-accessible medium 150, which may provide the instructions to the processing arrangement 140 to configure the processing arrangement 140 to execute certain exemplary procedures, processes and methods.

The applicator arrangement 130 according to this embodiment comprises at least one suitable composition application device for depositing a topical composition (e.g., a cosmetic composition and/or a skin treatment composition) onto frexels. In use, a user preferably holds the device 100 so that the applicator arrangement 130 is perpendicular or substantially perpendicular to the skin such that frexels toward which the applicator arrangement 130 will supply drops of the topical composition will map accurately to locations identified within the image to which the composition should be applied or so that this mapping is within a predetermined margin of error within which slight misalignments are not noticeable regardless of the morphology of the skin. An exemplary topical composition application device in this embodiment includes, for example, a sprayer (e.g., an electronic sprayer or airbrush sprayer), a drop control device, or any other suitable application device for applying a composition in small drops to desired locations as would be understood by those skilled in the art. In one exemplary embodiment, the applicator arrangement 130 comprises a nozzle for depositing a pressurized liquid or viscous composition in the form of a pressurized mist onto the skin to form a thin layer of coverage at a desired location. The nozzle may be any suitable device for depositing a thin layer of the composition onto aimed locations on the skin. In one exemplary embodiment, the nozzle may comprise dual chambers with a first chamber holding the liquid or viscous composition and a second chamber containing a propellant (e.g., compressed air or nitrogen gas) applying a pressure to, but not mixed with the composition when a pulse of the composition is dispensed to a frexel. In another example, the nozzle comprises a first chamber holding the liquid or viscous composition and a second chamber containing a propellant to be mixed with the composition when the composition is dispensed to a desired location. Although two exemplary embodiments of the nozzle are described above, it is contemplated that the device of the present application may include any suitable nozzle for dispensing droplets of the composition under pressure as would be understood by those skilled in the art.

The applicator arrangement 130 is operably connected to a reservoir 160 containing the topical composition to be applied to the skin. In particular, the applicator arrangement 130 is fluidly connected by a series of conduits, valves, and/or pressure sources to the reservoir 160. It is contemplated that the reservoir 160 may be housed anywhere within the device 100. In one exemplary embodiment, as shown in FIG. 1, the reservoir 160 is housed within the handle portion 104 of the device 100. The composition within the reservoir 160 is transferred from the reservoir 160 to the applicator arrangement 130 for deposition of the composition. In some embodiments, the reservoir 160 is a removeable container that can be replaced upon exhaustion of the contents therein. For example, the reservoir 160 may be a pressurized canister containing the composition to be applied to the skin therein.

The composition to be applied to the skin may comprise, for example, any suitable cosmetic ingredients for modifying an appearance of the skin, such as, for example, an opaque substance, a tinted cosmetic, or any other suitable compositions for enhancing the appearance of skin. The composition may also comprise ingredients such as a moisturizer for hydration, a carrier, or a benefit agent (e.g., a beneficial compound/composition/extract or an active ingredient) for treating and/or ameliorating a skin condition, e.g., acne, hyperpigmentation, eczema, hives, vitiligo, psoriasis, rosacea, warts, shingles, cold sore, pigmentation and tone, redness/oxidative skin stress, wrinkles, brightening, sagging/elasticity, etc. Exemplary embodiments of benefit agents that may be incorporated into the composition are further described below.

A non-limiting list of useful hydrating active benefit agents includes hyaluronic acid, and humectants. The hyaluronic acid may be linear, cross-linked, or a mixture of linear and cross-linked hyaluronic acid. It may be in a salt form, such as sodium hyaluronate. A humectant is a compound intended to increase the water content of the top layers of skin (e.g., hygroscopic compounds). Examples of suitable humectants include, but are not limited to, glycerin, sorbitol or trehalose or a salt or ester thereof.

A non-limiting list of useful benefit agents for acne includes benzoyl peroxide, retinoids including retinol, retinal, retinoic acid, retinyl acetate, and retinyl palmitate, hydroxy acids include, but are not limited, to glycolic acid, lactic acid, malic acid, salicylic acid, citric acid, and tartaric acid, sulfur, Zinc PCA (Zinc Pyrrolidone carboxylic acid), Allantoin (5-ureidohydantoin), Rosemary, 4-hexylresorcinol, N-acetyl glucosamine, gluconolactone, niacinamide, azelaic acid, and resveratrol.

A non-limiting list of useful pigmentation active benefit agents includes resorcinols, such as niacinamide, 4-hexyl resorcinol, curcuminoids (such as Sabiwhite (Tetrahydrocurcumin), phytic acid, resveratrol, soybean glycine soja oil, gluconolactone, azelaic acid, and retinoids including retinol, retinal, retinoic acid, retinyl acetate, and retinyl palmitate, enzymes such as laccase, tyrosinase inhibitors, melanin-degradation agents, melanosome transfer inhibiting agents including PAR-2 antagonists, exfoliants, sunscreens, retinoids, antioxidants, Tranexamic acid, tranexamic acid cetyl ester hydrochloride, skin bleaching agents, linoleic acid, adenosine monophosphate disodium salt, Chamomilla extract, allantoin, opacifiers, talcs and silicas, zinc salts, and the like. Examples of suitable tyrosinase inhibitors include but, are not limited to, Vitamin C and its derivatives, Vitamin E and its derivatives, Kojic Acid, Arbutin, resorcinols, hydroquinone, Flavones e.g., Licorice flavanoids, Licorice root extract, Mulberry root extract, Dioscorea Coposita root extract, Saxifraga extract and the like, Ellagic acid, Salicylates and derivatives, Glucosamine and derivatives, Fullerene, Hinokitiol, Dioic acid, Acetyl glucosamine, 5,5'-dipropyl-biphenyl-2,2'-diol (Magnolignan), 4-(4-hydroxyphenyl)-2-butanol (4-HPB), combinations of two or more thereof, and the like. Examples of vitamin C derivatives include, but are not limited to, ascorbic acid and salts, Ascorbic Acid-2-Glucoside, sodium ascorbyl phosphate, magnesium ascorbyl phosphate, and natural extract enriched in vitamin C. Examples of vitamin E derivatives include, but are not limited to, alpha-tocopherol, beta, tocopherol, gamma-tocopherol, delta-tocopherol, alpha-tocotrienol, beta-tocotrienol, gamma-tocotrienol, delta-tocotrienol and mixtures thereof, tocopherol acetate, tocopherol phosphate and natural extracts enriched in vitamin E derivatives. Examples of resorcinol derivatives include, but are not limited to, resorcinol, 4-substituted resorcinols like 4-alkyl-resorcinols such as 4-butyresorcinol (rucinol), 4-hexylresorcinol, phenylethyl resorcinol, 1-(2,4-dihydroxyphenyl)-3-(2, 4-dimethoxy-3-methylphenyl)-Propane and the like and natural extracts enriched in resorcinols. Examples of salicylates include, but are not limited to, 4-methoxy potassium salicylate, salicylic acid, acetylsalicylic acid, 4-methoxysalicylic acid and their salts. In certain preferred embodiments, the tyrosinase inhibitors include a 4-substituted resorcinol, a vitamin C derivative, or a vitamin E derivative A non-limiting list of useful redness/antioxidant active benefit agents includes water-soluble antioxidants such as sulfhydryl compounds and their derivatives (e.g., sodium metabisulfite and N-acetyl-cysteine), lipoic acid and dihydrolipoic acid, resveratrol, lactoferrin, and ascorbic acid and ascorbic acid derivatives (e.g., ascorbyl palmitate and ascorbyl polypeptide). Oil-soluble antioxidants suitable for use in the compositions of this invention include, but are not limited to, butylated hydroxytoluene, retinoids (e.g., retinol and retinyl palmitate), tocopherols (e.g., tocopherol acetate), tocotrienols, and ubiquinone. Natural extracts containing antioxidants suitable for use in the compositions of this invention, include, but not limited to, extracts containing flavonoids and isoflavonoids and their derivatives (e.g., genistein and diadzein), extracts containing resveratrol and the like. Examples of such natural extracts include grape seed, green tea, pine bark, propolis and extracts of feverfew. By "extracts of feverfew," it is meant extracts of the plant "Tanacetum parthenium," One particularly suitable feverfew extract is commercially available as about 20% active feverfew.

A non-limiting list of useful wrinkle active benefit agents includes N-acetyl glucosamine, 2-dimethylaminoethanol, copper salts such as copper chloride, peptides like argireline, syn-ake and those containing copper, coenzyme Q10, dill, blackberry, princess tree, picia anomala, and chicory, resorcinols, such as 4-hexyl resorcinol, curcuminoids and retinoids including retinol, retinal, retinoic acid, retinyl acetate, and retinyl palmitate, hydroxy acids include, but are not limited, to glycolic acid, lactic acid, malic acid, salicylic acid, citric acid, and tartaric acid.

A non-limiting list of useful brightening active benefit agents includes Vitamin C and its derivatives such as Ascorbic Acid 2-Glucoside, alpha-hydroxy acids such as lactic acid, glycolic acid, malic acid, tartaric acid, citric acid, or any combination of any of the foregoing, beta-hydroxy acids such as salicylic acid, polyhydroxy acids such as lactobionic acid and gluconic acid.

A non-limiting list of useful benefit agents for sagging skin includes blackberry extracts, cotinus extracts, feverfew extracts, extracts of *Phyllanthus niruri* and bimetal complexes having copper and/or zinc constituents. The bimetal complex having copper and/or zinc constituents may be, for example, copper-zinc citrate, copper-zinc oxalate, copper-zinc tartarate, copper-zinc malate, copper-zinc succinate, copper-zinc malonate, copper-zinc maleate, copper-zinc aspartate, copper-zinc glutamate, copper-zinc glutarate, copper-zinc fumarate, copper-zinc glucarate, copper-zinc polyacrylic acid, copper-zinc adipate, copper-zinc pimelate, copper-zinc suberate, copper-zinc azealate, copper-zinc sebacate, copper-zinc dodecanoate, or combinations thereof.

Additional skin benefit agents or actives may include those actives listed in the following paragraphs. While some of these actives may have been listed above, they are included below to ensure a more robust listing.

Examples of suitable additional benefit agents include: skin lightening agents, darkening agents, anti-aging agents, tropoelastin promoters, collagen promoters, anti-acne agents, shine control agents, anti-microbial agents such as anti-yeast agents, anti-fungal, and anti-bacterial agents, anti-inflammatory agents, anti-parasite agents, external analgesics, sunscreens, photoprotectors, antioxidants, keratolytic agents, detergents/surfactants, moisturizers, nutrients, vitamins, energy enhancers, anti-perspiration agents, astringents, deodorants, hair removers, hair growth enhancing agents, hair growth delaying agents, filming agents, hydration boosters, efficacy boosters, anti-callous agents, agents for skin conditioning, anti-cellulite agents, fluorides, teeth whitening agents, anti-plaque agents, and plaque-dissolving agents, odor-control agents such as odor masking or pH-changing agents, and the like. Examples of various suitable additional cosmetically acceptable actives include UV filters such as but not limited to avobenzone (Parsol 1789), bisdisulizole disodium (Neo Heliopan AP), diethylamino hydroxybenzoyl hexyl benzoate (Uvinul A Plus), ecamsule (Mexoryl SX), methyl anthranilate, 4-aminobenzoic acid (PABA), cinoxate, ethylhexyl triazone (Uvinul T 150), homosalate, 4-methylbenzylidene camphor (Parsol 5000), octyl methoxycinnamate (Octinoxate), octyl salicylate (Octisalate), padimate O (Escalol 507), phenylbenzimidazole sulfonic acid (Ensulizole), polysilicone-15 (Parsol SLX), trolamine salicylate, Bemotrizinol (Tinosorb S), benzophenones 1-12, dioxybenzone, drometrizole trisiloxane (Mexoryl XL), iscotrizinol (Uvasorb HEB), octocrylene, oxybenzone (Eusolex 4360), sulisobenzone, bisoctrizole (Tinosorb M), titanium dioxide, zinc oxide, carotenoids, free radical scavengers, spin traps, retinoids and retinoid precursors such as retinol, retinoic acid and retinyl palmitate, ceramides, polyunsaturated fatty acids, essential fatty acids, enzymes, enzyme inhibitors, minerals, hormones such as estrogens, steroids such as hydrocortisone, 2-dimethylaminoethanol, copper salts such as copper chloride, peptides containing copper such as Cu:Gly-His-Lys, coenzyme Q10, amino acids such a proline, vitamins, lactohionic acid, acetyl-coenzyme A, niacin, riboflavin, thiamin, ribose, electron transporters such as NADH and FADH2, and other botanical extracts such as oat, aloe vera, Feverfew, Soy, Shiitake mushroom extracts, and derivatives and mixtures thereof.

Examples of suitable skin lightening benefit agents include, but are not limited to, tyrosinase inhibitors, melanin-degradation agents, melanosome transfer inhibiting agents including PAR-2 antagonists, exfoliants, sunscreens, retinoids, antioxidants, Tranexamic acid, tranexamic acid cetyl ester hydrochloride, skin bleaching agents, linoleic acid, adenosine monophosphate disodium salt, Chamomilla extract, allantoin, opacifiers, talcs and silicas, zinc salts, and the like.

Examples of suitable tyrosinase inhibitors include but, are not limited to, Vitamin C and its derivatives, Vitamin E and its derivatives, Kojic Acid, Arbutin, resorcinols, hydroquinone, Flavones e.g. Licorice flavanoids, Licorice root extract, Mulberry root extract, Dioscorea Coposita root extract, Saxifraga extract and the like, Ellagic acid, Salicylates and derivatives, Glucosamine and derivatives, Fullerene, Hinokitiol, Dioic acid, Acetyl glucosamine, 5,5'-dipropyl-biphenyl-2,2'-diol (Magnolignan), 4-(4-hydroxyphenyl)-2-butanol (4-HPB), combinations of two or more thereof, and the like. Examples of vitamin C derivatives include, but are not limited to, ascorbic acid and salts, Ascorbic Acid-2-Glucoside, sodium ascorbyl phosphate, magnesium ascorbyl phosphate, and natural extract enriched in vitamin C. Examples of vitamin E derivatives include, but are not limited to, alpha-tocopherol, beta, tocopherol, gamma-tocopherol, delta-tocopherol, alpha-tocotrienol, beta-tocotrienol, gamma-tocotrienol, delta-tocotrienol and mixtures thereof, tocopherol acetate, tocopherol phosphate and natural extracts enriched in vitamin E derivatives. Examples of resorcinol derivatives include, but are not limited to, resorcinol, 4-substituted resorcinols like 4-alkyl-resorcinols such as 4-butyresorcinol (rucinol), 4-hexylresorcinol (Synovea HR, Sytheon), phenylethyl resorcinol (Symwhite, Symrise), 1-(2,4-dihydroxyphenyl)-3-(2,4-dimethoxy-3-methylphenyl)-Propane (nivitol, Unigen) and the like and natural extracts enriched in resorcinols. Examples of salicylates include, but are not limited to, 4-methoxy potassium salicylate, salicylic acid, acetylsalicylic acid, 4-methoxysalicylic acid and their salts. In certain preferred embodiments, the tyrosinase inhibitors include a 4-substituted resorcinol, a vitamin C derivative, or a vitamin E derivative. In more preferred embodiments, the tyrosinase inhibitor comprises Phenylethyl resorcinol, 4-hexyl resorcinol, or ascorbyl-2-glucoside.

Examples of suitable melanin-degradation agents include, but are not limited to, peroxides and enzymes such as peroxidases and ligninases. In certain preferred embodiments, the melanin-inhibiting agents include a peroxide or a ligninase.

Examples of suitable melanosome transfer inhibiting agents including PAR-2 antagonists such as soy trypsin inhibitor or Bowman-Birk Inhibitor, Vitamin B3 and derivatives such as Niacinamide, Essential soy, Whole Soy, Soy extract. In certain preferred embodiments, the melanosome transfer inhibiting agents includes a soy extract or niacinamide.

Examples of exfoliants include, but are not limited to, alpha-hydroxy acids such as lactic acid, glycolic acid, malic acid, tartaric acid, citric acid, or any combination of any of the foregoing, beta-hydroxy acids such as salicylic acid, polyhydroxy acids such as lactobionic acid and gluconic acid, and mechanical exfoliation such as microdermabrasion. In certain preferred embodiments, the exfoliant include glycolic acid or salicylic acid.

Examples of sunscreens include, but are not limited to, avobenzone (Parsol 1789), bisdisulizole disodium (Neo Heliopan AP), diethylamino hydroxybenzoyl hexyl benzoate (Uvinul A Plus), ecamsule (Mexoryl SX), methyl anthranilate, 4-aminobenzoic acid (PABA), cinoxate, ethylhexyl triazone (Uvinul T 150), homosalate, 4-methylbenzylidene camphor (Parsol 5000), octyl methoxycinnamate (Octinoxate), octyl salicylate (Octisalate), padimate O (Escalol 507), phenylbenzimidazole sulfonic acid (Ensulizole), polysilicone-15 (Parsol SLX), trolamine salicylate, Bemotrizinol (Tinosorb S), benzophenones 1-12, dioxybenzone, drometrizole trisiloxane (Mexoryl XL), iscotrizinol (Uvasorb HEB), octocrylene, oxybenzone (Eusolex 4360), sulisobenzone, bisoctrizole (Tinosorb M), titanium dioxide, zinc oxide, and the like.

Examples of retinoids include, but are not limited to, retinol (Vitamin A alcohol), retinal (Vitamin A aldehyde), retinyl acetate, retinyl propionate, retinyl linoleate, retinoic acid, retinyl palmitate, isotretinoin, tazarotene, bexarotene, Adapalene, combinations of two or more thereof and the like. In certain preferred embodiments, the retinoid is selected from the group consisting of retinol, retinal, retinyl acetate, retinyl propionate, retinyl linoleate, and combinations of two or more thereof. In certain more preferred embodiments, the retinoid is retinol.

Examples of antioxidants include, but are not limited to, water-soluble antioxidants such as sulfliydryl compounds and their derivatives (e.g., sodium metabisulfite and N-acetyl-cysteine, glutathione), lipoic acid and dihydrolipoic acid, stilbenoids such as resveratrol and derivatives, lactoferrin, iron and copper chelators and ascorbic acid and ascorbic acid derivatives (e.g., ascobyl-2-glucoside, ascorbyl palmitate and ascorbyl polypeptide). Oil-soluble antioxidants suitable for use in the compositions of this invention include, but are not limited to, butylated hydroxytoluene, retinoids (e.g., retinol and retinyl palmitate), tocopherols (e.g., tocopherol acetate), tocotrienols, and ubiquinones. Natural extracts containing antioxidants suitable for use in the compositions of this invention, include, but not limited to, extracts containing flavonoids and isoflavonoids and their derivatives (e.g., genistein and diadzein), extracts containing resveratrol and the like. Examples of such natural extracts include grape seed, green tea, black tea, white tea, pine bark, feverfew, parthenolide-free feverfew, oat extracts, blackberry extract, cotinus extract, soy extract, pomelo extract, wheat germ extract, Hesperedin, Grape extract, Portulaca extract, Licochalcone, chalcone, 2,2'-dihydroxy chalcone, Primula extract, propolis, and the like.

In some preferred embodiments, useful benefit agents for acne include, but are not limited, salicylic acid, Zinc PCA (Zinc Pyrrolidone carboxylic acid), Allantoin (5-ureidohydantoin), Rosemary, 4-hexylresorcinol, N-acetyl glucosamine, gluconolactone, niacinamide, azelaic acid, and resveratrol.

In some preferred embodiments, a list of useful pigmentation active benefit agents includes tetrahydrocurcumin, phytic acid, resveratrol, soybean glycine soja oil, gluconolactone, laccase, 4-hexyl resorcinol, N-acetyl glucosamine, gluconolactone, niacinamide, azelaic acid, and resveratrol.

In some preferred embodiments, a list of useful active benefit agents includes to simultaneously treat acne and pigmentation includes 4-hexyl resorcinol, N-acetyl glucosamine, gluconolactone, niacinamide, azelaic acid, and resveratrol.

The composition may be a cosmetic composition (which may or may not include additional active ingredients for the treatment of skin) that is applied to the skin to alter or minimize the appearance of an artifact based on the image data supplied by the detector arrangement 120. In one particular embodiment, the composition comprises one or more reflectance modifying agents (RMAs) (any component useful for altering reflectance of the skin). For example, suitable RMAs may include inks, dyes, pigments, bleaching agents, chemically altering agents and other substances that may be used to alter the reflectance of the skin. Some suitable RMAs may include a transparent RMA, such as a dye or a diluted pigment. Other suitable RMAs may include an opaque RMA having high refractive index particles. In particular, the high refractive index particles may comprise particles having a refractive index of 2.0 or greater. In one specific example, the RMA may comprise particles of titanium dioxide. Specifically, the titanium dioxide particles may be uniformily distributed and/or suspended in the cosmetic composition.

The device 100 according to this embodiment further comprises a power source 170 providing power to control and operate the device 100. It is contemplated that the power source 170 may be located anywhere within the device 100 or may alternatively be external to the device 100. In one exemplary embodiment, as shown in FIG. 1, the power source 170 which is housed within the handle portion 104 of the device 100, is operably connected to the optical emitter 110, the detector arrangement 120, the applicator arrangement 130 and/or the processing arrangement 140. Those skilled in the art will understand that various known suitable sources of power may be used. For example, the power source 170 may comprise a battery or a connection to an external source of power. In particular, the power source 170 may comprise a rechargeable battery device.

As discussed above, the device and method of the present application utilizes fiducials projected by the optical emitter 110 to adjustably align the image captured by the detector arrangement 120 with a location on the skin aimed by the applicator arrangement 130. For example, the optical emitter 110 may be positioned at an angle to the detector arrangement 120 and/or the applicator arrangement 130. Therefore, as illustrated in Example I below, fiducials projected by the optical emitter 110 onto a surface of skin would mark the skin at different locations, depending on a distance between the optical emitter 110 and the skin and an angle of the optical emitter 110 to a surface of the skin. As a result, the fiducials are captured by the detector arrangement 120 at different regions within an image of the skin, depending on the distance between the optical emitter 110 and the skin. Therefore, the fiducials can be used to generate fiducial calibration data correlating regions within an image captured by the detector arrangement 120 to the morphology of the skin.

More particularly, the fiducial calibration data correlates regions within fiducial calibration images of a substrate captured by the detector arrangement 120 with distances between the optical emitter 110 and a calibration substrate for each one of the fiducials. For example, the fiducial calibration data may be obtained empirically using a calibration substrate having a flat or substantially flat surface and, preferably, having gridded guidelines, such, as for example, a piece of graph paper. The calibration substrate, marked with fiducials projected from the optical emitter 110, can be imaged by the detector arrangement 120 from a plurality of known distances to generate data corresponding to fiducial calibration images and provide fiducial calibration data to generate a correlation between the regions marked by each of the fiducials in the fiducial calibration images and the known calibration distances, as further illustrated, for example, below in Example II. While a minimum of two known distances are needed to generate the correlation (e.g., a linear correlation), three or more known distances may be used to generate more precise and accurate fiducial calibration data and further align the distances and regions marked by each of the fiducials in the fiducial calibration images to adjust for additional sources of distortions (e.g., lens distortion from the detector arrangement 120).

The fiducial calibration data can include empirically measured fiducial calibration data. In some embodiments, the fiducial calibration data may include data interpolated from the empirical data to form a resolution matrix correlating select regions within fiducial calibration images with interpolated distances between the optical emitter 110 and the substrate. More particularly, the fiducial calibration data may comprise data interpolated from the empirical data to form a look-up table correlating every pixel within the fiducial calibration images with a distance, for each one of the fiducials. The processing arrangement 140 analyzes image data for an image of the skin received from the detector arrangement 120 to determine a morphology of the skin by comparing the image data to the fiducial calibration data. The look-up table may provide a more expedient way for the processing arrangement 140 to compare the image data to the fiducial calibration data because real-time or near real-time interpolation of the fiducial calibration data would not be necessary.

As discussed above, image data obtained by the detector arrangement 120 may be distorted by the angled positioning of the detector arrangement 120. Similarly, a composition applied by the application arrangement 130 may land on a frexel different from one for which it was intended if a distance between the applicator arrangement 130 and the skin is not accounted for, as illustrated further below in Example I. Therefore, the composition applied by the application arrangement 130 is also captured by the detector arrangement 120 at different regions within an image of the skin, depending on the morphology of the skin.

The processing arrangement 140 can use the morphology determined from the image data to identify a region within the image captured by the detector arrangement 120 that corresponds to a frexel aimed by the applicator arrangement 130. For example, the region may be identified by comparing the determined morphology to applicator calibration data correlating the morphology of the skin to regions within one or more images captured by the detector arrangement 120 that correspond to a deposition of the composition from the applicator arrangement 130. For example, the applicator calibration data correlates distances between the applicator arrangement 130 and a substrate (e.g., the skin) with regions within applicator calibration images of the calibration substrate captured by the detector arrangement 120. For example, the applicator calibration can be generated in a manner similar to that discussed above for the fiducial calibration data. Specifically, the applicator arrangement 130 deposits a composition to a calibration substrate, having a flat or substantially flat surface and, preferably, having gridded guidelines, such, as for example, a piece of graph paper, placed at a known distance from the detector arrangement 120, and the detector arrangement 120 subsequently images the calibration substrate having the composition to generate data corresponding to an applicator calibration image. This applicator calibration process may be performed using two or more known distances to generate data corresponding to a plurality of applicator calibration images and provide applicator calibration data correlating the distances with regions corresponding to a deposition of the composition captured in the applicator calibration images, in a similar manner as discussed above for the fiducial calibration data and as explained further below in Example II. Similar to the fiducial calibration data, the applicator calibration data may comprise empirically measured data or may include data interpolated based on the empirically measured data, such as, for example, a resolution matrix correlating select regions within applicator calibration images with interpolated distances between the applicator arrangement 130 and the substrate and/or a look-up table correlating every pixel within the applicator calibration images with a distance.

The fiducial calibration data and/or applicator calibration data may be generated prior to an initial use of the device 100 or may be generated before a session of use, conducted in multiple passes across a portion of skin. The fiducial calibration data and/or applicator calibration data may be stored on the computer-accessible medium 150 or a storage arrangement separate from the computer-accessible medium 150 that is located within or external to the device 100. The processing arrangement 140 is operably connected to the computer-accessible medium 150 or to the separate storage arrangement to retrieve the fiducial calibration data and/or applicator calibration data therefrom.

In use, the head portion 102 is placed over an area of skin to be treated. During use, the device 100 may be utilized to image a plurality of different areas of skin. For example, the head portion 102 may be moved across a surface of the skin allowing the device 100 to continuously image (at any desired frame rate) different areas of the skin to obtain image data and analyze the image data to selectively apply the composition to desired frexels (locations on the skin). More particularly, the user may move the head portion 102 back and forth across the surface of the skin in multiple passes to allow the device 100 to review previously treated areas to detect artifacts which were missed or incompletely addressed and apply the composition to identified artifacts on the skin.

Figure 2:
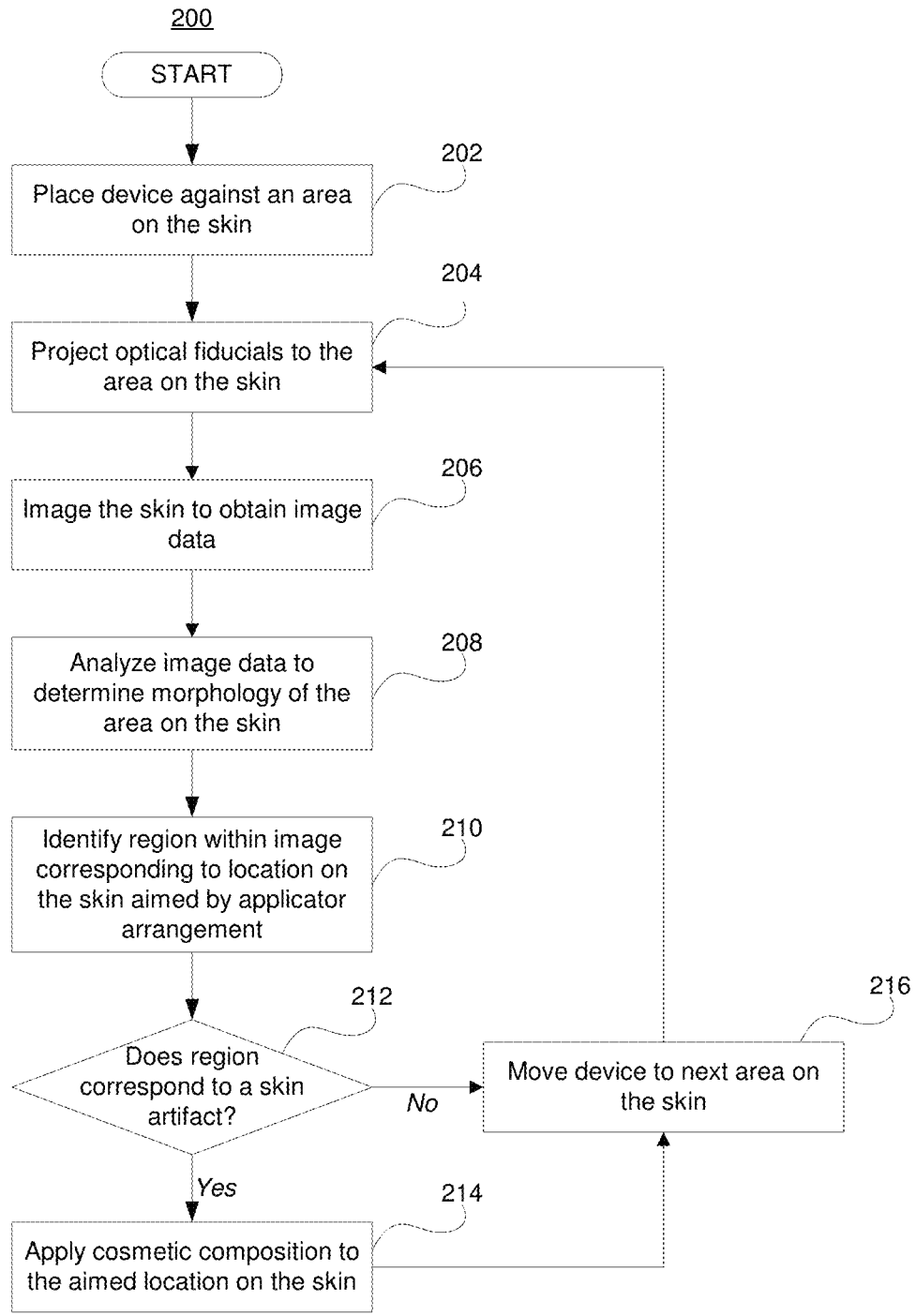
FIG. 2 shows an exemplary method for selectively applying a topical composition to the skin of a user, according to an exemplary embodiment of the present application.

The present application also includes a method for selectively applying a composition to the skin. An exemplary method 200 is shown in FIG. 2. In step 202, the user may initiate use of the device 100 by placing a head portion 102 of the device 100 against a surface of skin, for example, the skin of the face. The head portion 102 covers an area of skin, e.g., an area constituting a frame to be imaged and analyzed by the device 100. As indicated in step 204, the optical emitter 110 projects fiducials onto the area of skin over which the device 100 is placed, as discussed above. In step 206, the detector arrangement 120 images the area to obtain image data for the area of the skin on which fiducials have been projected. In step 208, the processing arrangement 140 analyzes the image data from the detector arrangement 120 to determine a morphology of the area of skin over which the device 100 is placed. In particular, the processing arrangement 140 analyzes the image data and determines the morphology of the area of skin by comparing the image data to fiducial calibration data. For example, the processing arrangement 140 determines, for each fiducial, a distance between the optical emitter 110 and a height of the location on the skin on which the fiducial has been projected using a correlation provided by the fiducial calibration data.

It is also contemplated that step 208 may include steps to further adjust, manipulate, and/or process the image data under various conditions so as to reduce distortions to the fiducials caused by variations in the color and texture of the skin, using various techniques, such as for example, those exemplary methods discussed below in Example IV. The morphology of the area of skin over which the device 100 is placed may be obtained by analyzing this further processed data. In one example, the image data, which correspond to an image of an area of the skin marked with fiducials, may be adjusted using a secondary set of image data corresponding to an image of the same area captured by the detector arrangement 120 without fiducial markings. The adjusted image data may be subsequently analyzed to determine a morphology of the area of skin over which the device 100 is placed. In some embodiments, the image data may be obtained using a first sensor for detecting light in a first color and the secondary set of image data may be obtained using a second sensor for detecting light in a second color.

In step 210, the processing arrangement 140 uses the morphology determined in step 208 to identify within the image obtained by the detector arrangement 120 in step 206 a location that corresponds to an aimed location of the applicator arrangement 130 (i.e., a frexel or frexels to which a drop emitted from each composition applying nozzle of the applicator arrangement 130 would be applied in the current alignment of the device relative to the skin). In particular, the processing arrangement 140 identifies the regions to which the composition would be applied by the applicator arrangement 130 by comparing the morphology to applicator calibration data, as further illustrated, for example, below in Example III.

In step 212, the processing arrangement 140 further analyzes the image data to determine whether the region within the image obtained by the detector arrangement 120 identified in step 210 contains a skin artifact having a magnitude that warrants the application of the composition (i.e., a magnitude greater than a predetermined threshold level). As would be understood by those skilled in the art, image data corresponding to the identified region can be analyzed by the processing arrangement 140 using any suitable methods, to identify artifacts. For example, image data for the identified region may be analyzed by the processing arrangement 140 to determine if the region represents a skin artifact whose appearance should be altered by comparing a reflectance captured in the identified region of the image to an average reflectance in the entire image. It is also contemplated that the processing arrangement 140 can utilize additional data, including the morphology determined in step 208, to determine if the region represents a skin artifact. In one exemplary embodiment of step 212, a region identified as having a reflectance that significantly deviates from an average reflectance of the entirety of its associated image frame is determined to correspond to a skin artifact. In another exemplary embodiment, image data corresponding to the region identified in step 210 is analyzed by the processing arrangement 140 to determine whether image data corresponding to the region identified in step 210 includes spectral components within the range of middle spatial frequencies for the entire frame of skin imaged (i.e., the image obtained by the detector arrangement in step 206) that have an elevated intensity relative to the balance of the image. Locations at which an intensity in the middle spatial frequencies is above a threshold level are identified as artifacts to which the cosmetic composition should be applied. Preferably, the range of middle spatial frequencies is determined for each frame based on a reflectance of the entire imaged area.

Those locations that include intense contributions in the middle spatial frequencies of an image may, for example, include artifacts whose appearance a user may wish to alter or minimize. The middle spatial frequencies are believed to contribute a small percentage (e.g., around 5%) to the overall spatial frequency of an image of skin and/or visual perception of the skin. However, it is believed that spatial frequency components within the middle spatial frequencies are particularly visually noticeable and therefore, provide a disproportionally larger image to the perceived aesthetic appearance of the skin. Therefore, it is believed that altering or minimizing the appearance of skin by selectively applying a topical composition to those frexels corresponding to details within the middle spatial frequencies of an image of the skin would impart an aesthetic pleasing appearance to the skin. It may be particularly beneficial to selectively alter or minimize the appearance of only those frexels that correspond to middle spatial frequencies to provide a visually noticeable aesthetic change to the appearance of skin while modifying only a limited number of frexels on the skin. Therefore, a reduced amount of topical composition may be applied to the skin while still providing an aesthetically noticeable improvement to the appearance of skin. Additional devices and methods for detecting artifacts using reflectance and analysis of middle spatial frequencies are described in, for example, U.S. Pat. Nos. 8,007,062, 9,020,184 and 10,092,082, the disclosures of which are incorporated by reference herein.

If a skin artifact is detected in step 212, then the methods proceeds to step 214. In step 214, the processing arrangement 140 directs the applicator arrangement 130 to apply the topical composition to the location of the artifact(s) identified in the imaged area of skin. If a skin artifact is not detected in step 212, the method 200 does not apply any topical composition to any location within the imaged region of skin and the method proceeds to step 216. In step 216, the device 100 is moved by the user to a new frame or area of the skin and the process is repeated. This movement may be detected by the device 100 by any suitable means, such as, for example, an accelerometer or image analysis. The method 200 then returns to step 204 and projects fiducials, images, analyzes and selectively applies the topical composition, as determined by the device 100, to this new area of skin in the same manner described above. It is noted that the method 200 may be interrupted and terminated by the user before any one of steps 204 through 216 by any suitable operation, such as, for example, removing the device 100 from the skin or switching off the device 100, in particular, the power source 170 of the device.

Those skilled in the art will understand that the exemplary embodiments described herein may be implemented in any number of manners, including as a separate software module, as a combination of hardware and software, etc. For example, the exemplary methods may be embodiment in one or more programs stored in a non-transitory storage medium and containing lines of code that, when compiled, may be executed by one or more processor cores or a separate processor. A system according to one embodiment comprises a plurality of processor cores and a set of instructions executing on the plurality of processor cores to perform the exemplary methods discussed above. The processor cores or separate processor may be incorporated in or may communicate with any suitable electronic device, for example, on board processing arrangements within the device or processing arrangements external to the device, e.g., a mobile computing device, a smart phone, a computing tablet, a computing device, etc., that may be in communications with at least a portion of the device.

EXAMPLES

Example I

Figure 3:
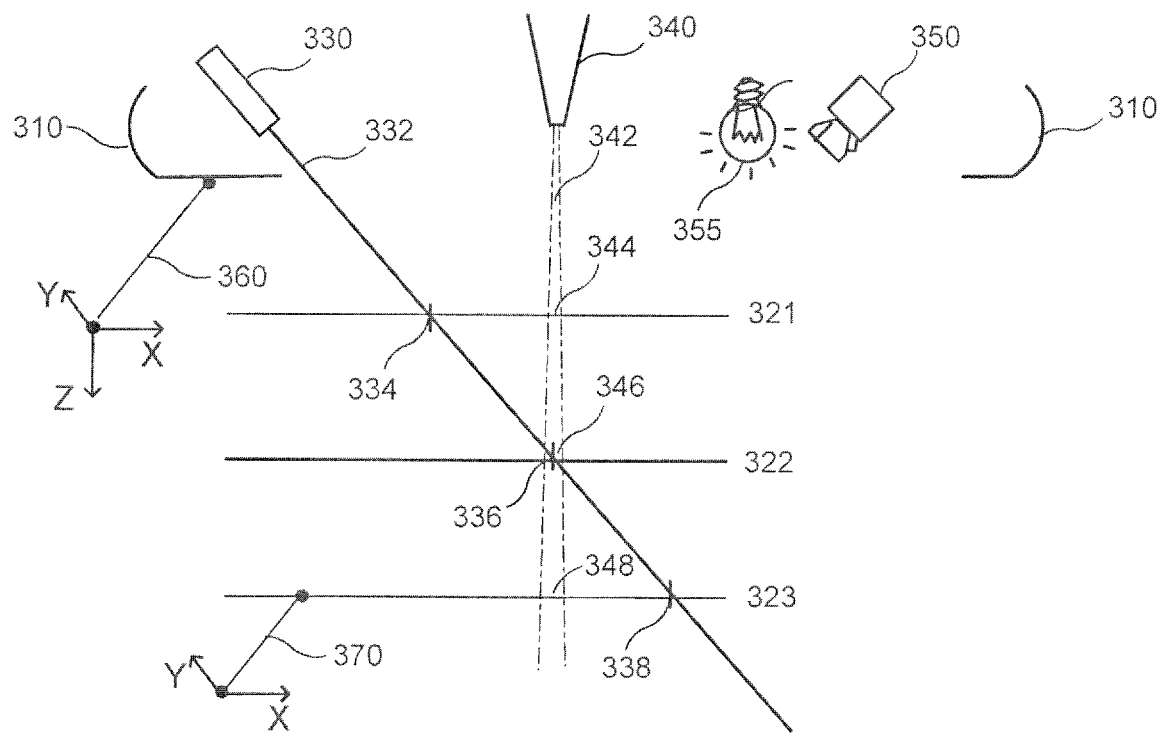
FIG. 3 shows another exemplary embodiment of a device for applying a composition to a substrate, according to Example I of the present application.
Figure 4:
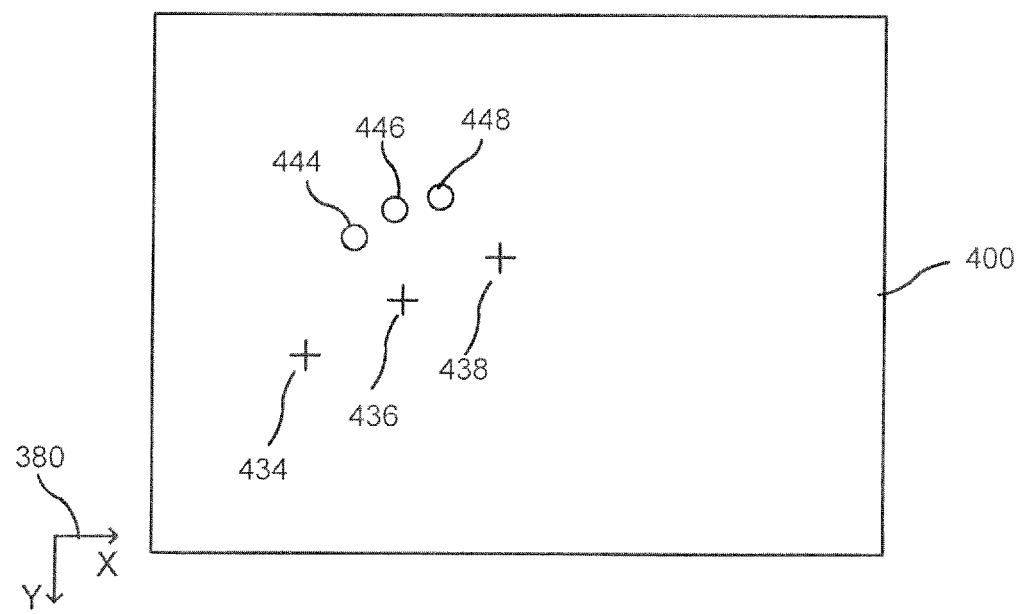
FIG. 4 shows an exemplary image that could be obtained by a camera of the exemplary device of FIG. 3.

Example I is provided to demonstrate alignment of a cosmetic spray and a camera guided with projected fiducials in a device that is placed at varying distances away from a flat surface of a substrate (e.g., skin). FIG. 3 shows an exemplary embodiment of a probe 310 within an exemplary device that when the device is placed over an area of skin to be treated, the probe 310 is not in direct contact with the skin. The probe 310 comprising an optical emitter 330 projecting at least one optical fiducial 332 to a flat surface of skin, a cosmetic applicator 340 for delivering a spray of cosmetic 342, and a camera 350. The exemplary probe 310 contains a light source 355 to illuminate the skin for the camera 350. In use, the exemplary probe 310 may be positioned over an area skin. As an illustration, different degrees of distance between the probe 310 and a flat surface of skin are shown, for example, in FIG. 3: a short distance 321, a medium distance 322, and a long distance 323. An exemplary image 400 that may be captured by the camera 350 is illustrated in FIG. 4.

As shown in FIG. 3, the optical emitter 330 is mounted at an angle to the skin and, therefore, an optical fiducial 332 projected to skin located at varying distances away from the probe 310 would mark the skin at different locations on the skin, which in turn results in the fiducial being captured at different positions within the image 400, depending on a distance between the probe 310 and the skin. For example, if the skin is located a short distance 321 from the probe 310, the projected fiducial 332 would mark the skin at position 334. This fiducial mark at position 334 on the skin can be captured by the camera at pixel 434 in the image 400 shown in FIG. 4. In another example, if the skin is located a medium distance 322 from the probe 310, the projected fiducial 332 would mark the skin at position 336. The fiducial mark at position 336 on the skin can be captured by the camera at pixel 436 in the image 400. In a further example, if the skin is located a long distance 323 from the probe 310, the projected fiducial 332 would mark the skin at position 338. The fiducial mark at position 338 on the skin can be captured by the camera at pixel 438 in the image 400.

As shown in FIG. 3, for example, a spray of cosmetic 342 delivered by a cosmetic applicator 340 would be aimed at position 344 for skin located a short distance 321 from the probe 310. As another example, the spray of cosmetic 342 would be aimed at position 346 for skin located a medium distance 322 from the device. As a further example, the spray of cosmetic 342 would be aimed at position 348 for skin located a long distance 323. In the exemplary embodiment shown in FIG. 3, the cosmetic applicator 340 is positioned perpendicular to and therefore, dispenses a spray of cosmetic in a direction perpendicular to the skin. Therefore, a cosmetic applicator 340 positioned perpendicular to the skin would dispense the cosmetic at the same location on the two-dimensional surface of the skin, regardless of the distance between the probe 310 and the skin. However, if the cosmetic applicator 340 is positioned at an angle to the surface of the skin, the cosmetic would be applied to different locations on the skin.

Although the cosmetic applicator 340 is positioned perpendicular to the skin and aims at the same location on the two-dimensional surface of the skin independent of the distance between the probe 310 and the skin, the camera 350 is mounted at an angle to the cosmetic applicator 340 and the surface of the skin, and therefore may provide distortion to the captured image depending on the distance between the probe 310 and the skin. Additional distortions within an image captured by camera 350 may be attributed to camera lens distortion. For example, cosmetic applied to position 344 may be captured by the camera 350 at pixel 444 in the image 400 shown in FIG. 4. Similarly, cosmetic applied to positions 346 and 348 may be captured by the camera at pixels 446 and 448, respectively.

Example II

In Example II, to illustrate an exemplary calibration of regions within images captured by the camera 350 with distances a substrate is positioned from the probe 310, a device coordinate system 360, a skin frexel coordinate system 370, and a pixel coordinate system 380 are described herein. The device coordinate system 360, as shown in FIG. 3, corresponds to three-dimensional positioning of the probe 310. As shown in FIG. 3, the positions of the camera 350, optical emitter 330, and the cosmetic applicator 340 are fixed within this device coordinate system 360. This device coordinate system 360 includes position X and height Z axes as shown in FIG. 3, and a position Y axis extending perpendicularly from the X-Z plane as shown in FIG. 3. The skin frexel coordinate system 370, as shown in FIG. 3, corresponds to two-dimensional positioning across a surface of the skin. This skin frexel system 370 includes position X and position Y axes as shown in FIG. 3. In this example, because the cosmetic applicator 340 is positioned perpendicular to the skin, the X and Y axes of the skin frexel system 370 coincide with the X and Y axes of the device coordinate system 360 described above. The pixel coordinate system 380 as shown in FIG. 4, corresponds to two-dimensional positioning across an image frame of the camera 350. This pixel coordinate system 380 includes position X and position Y axes as shown in FIG. 4 corresponding to two-dimensional positioning of pixels across an image 400 captured by the camera 350.

In this example, the device is arranged similarly to Example I above, but the distances 321, 322 and 323 as shown in FIG. 3 are instead known distances for generating fiducial calibrations images of a calibration substrate for providing a correlation between the distances and regions within the calibration images for fiducial 332. A calibration substrate having gridded guidelines (e.g., a piece of graph paper) can be imaged by the camera 350 from distances 321, 322 and 323 to generate empirical fiducial calibration data corresponding to fiducial calibration images. As discussed above in Example I, the fiducial 332 projected to a substrate located a short distance 321 from the probe 310 would be captured by the camera at pixel 434 in the image 400. Similarly, the fiducial 332 projected to a substrate located a medium distance 322 and a long distance 323 from the probe 310 would be captured by the camera at pixel 436 and pixel 438 in the image 400, respectively. A location on the calibration substrate for each fiducial calibration image may be determined using the gridded guidelines. Therefore, a location on the calibration substrate marked by fiducial 332 (as indicated along the X and Y axes of the skin frexel coordinate system 370, which in this example also coincide with the X and Y axes of the device coordinate system 360) can be ascertained using the gridded guidelines. A distance between the height of the location on the calibration substrate marked by fiducial 332 and the probe 310 (as indicated in the Z axis of the device coordinate system 360) corresponds to the known distance (e.g., distance 321, 322 or 323) used to generate data corresponding to the fiducial calibration image. Therefore, if image data for an image of an area of skin captured by the camera 350 shows the fiducial 332 at pixel 434 within the image 400 (as indicated along the X and Y axes of the pixel coordinate system 380), the image data can be compared to the empirical fiducial calibration data to determine a position within the Z axis of the device coordinate system 360 for the location marked by the fiducial 332. The pixels within image 400 may optionally be further calibrated to positions within the X and Y axes of the skin frexel coordinate system 370 for the location marked by fiducial 332.

Figure 5A:
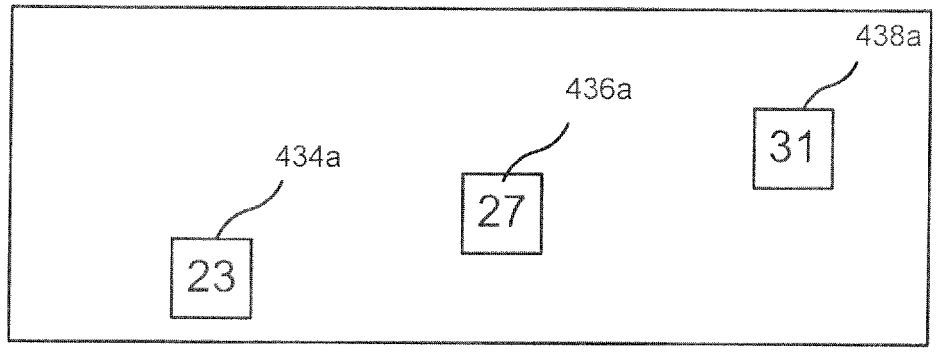
FIG. 5a shows an exemplary set of calibration data obtained according to Example II of the present application.
Figure 5B:
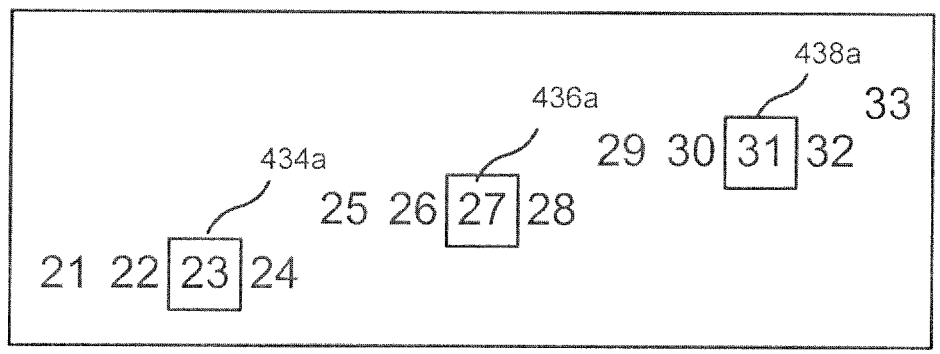
FIG. 5b shows another exemplary set of calibration data including the data of FIG. 5a along with additional interpolated datapoints, obtained according to Example II of the present application.
Figure 5C:
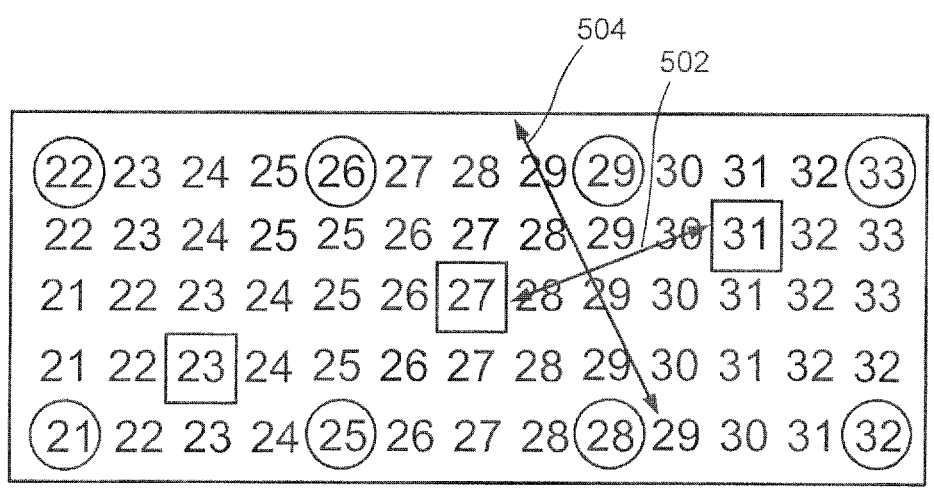
FIG. 5c shows a further exemplary set of calibration data having a look-up table correlating each pixel within an image to a distance between an optical emitter to a height of the skin marked by a fiducial projected by the optical emitter, obtained according to Example II of the present application.

In this example, three known distances are used to generate empirical fiducial calibration data and therefore, empirically calibrating three pixels within a fiducial calibration image captured by the camera 350 to the three known distances used for calibration. As shown in FIG. 5a, the three pixels 434, 436, and 438 in the image 400 may correspond to calibration data entries 434a, 436a, and 438a, respectively, and may each be correlated to the known distance used for calibration (e.g., in the Z-axis of the device coordinate system 360). The numerical values shown in FIG. 5a are exemplary for the purpose of illustrating the fiducial calibration data described herein and do not necessary correlate to any particular units of measurement. For example, pixel 434 is correlated to data entry 434a corresponding to the short distance 321, which is shown in FIG. 5a as having a value in the Z-axis of the device coordinate system 360 of "23." Pixel 436 is also correlated to data entry 436a corresponding to the medium distance 322, which is shown as having a Z-axis value in the device coordinate system 360 of "27." Similarly, pixel 438 is correlated data entry 438*a* corresponding to the long distance 323, which is shown as having a Z-axis value in the device coordinate system 360 of "31." The empirical data may be interpolated to correlate a distance to each pixel within the image. FIGS. 5*b* and 5*c* show an exemplary interpolation of calibration data entries for additional pixels along an interpolation line 502 or spline defined by the empirically calibrated pixels 434, 436 and 438 of image 400. FIG. 5*c* shows that distances corresponding to further pixels can, for example, be interpolated in a direction 504 perpendicular to the interpolation line 502 or spline to further correlate a distance to each pixel within the image. The fully interpolated correlation for each pixel within the image may be stored in the form of a look-up table as the fiducial calibration data within a storage medium. Alternatively, because the values may generally be linearly interpolated, a reduced resolution matrix correlating distances, for example, only to those pixels circled in FIG. 5*c* may be stored in the storage medium as the fiducial calibration data.

Although this example shows calibration of a single projected fiducial 332, a plurality of fiducials may be used to generate fiducial calibration data for more points within the X, Y and Z axes of the device coordinate system 360, which can be used to map the morphology, for example, tilt and/or curvature, of the skin. Each additional fiducial may be calibrated to correlate a different set of distances to each pixel within an image captured by the camera 350.

The cosmetic applicator 340 may also be calibrated in a similar manner as discussed above for the fiducial 332. The cosmetic applicator 340 deposits a cosmetic composition to a calibration substrate placed at each of distances 321, 322 and 323. The calibration substrates, bearing the cosmetic composition applied to the substrates, are imaged by the camera 350 from their respective distances to generate empirical applicator calibration data corresponding to applicator calibration images. Specifically, as discussed above in Example I, cosmetic applied to a substrate located a short distance 321 from the probe 310 is captured by the camera 350 at pixel 444, cosmetic applied to the substrate located a medium distance 322 from the probe 310 is captured by the camera 350 at pixel 446, and cosmetic applied to the substrate located a long distance 323 from the probe 310 is captured by the camera 350 at pixel 448. The empirically obtained applicator calibration data may also be interpolated to generate additional applicator calibration data correlating distances to additional pixels within the applicator calibration images in similar manners as discussed above for the fiducial 332.

Example III

Figure 6:
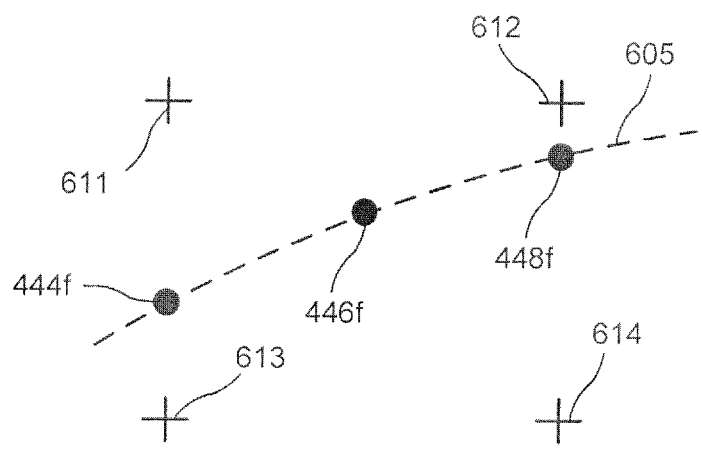
FIG. 6 shows an exemplary image frame for a camera showing application calibration data superimposed to pixels corresponding to fiducial marks captured in an exemplary image by the camera of an exemplary area of skin having a certain morphology, according to Example III of the present application.

Example III illustrates an exemplary method for identifying a region in an image captured by the camera 350 corresponding to an aimed location of the applicator 340. FIG. 6 shows an exemplary image frame for the camera 350. The image frame of FIG. 6 includes pixels 444*f*, 446*f*, and 448*f*, which are at the same positions within the image frame as pixels 444, 446 and 448 of image 400 from the applicator calibration data discussed above in Example II. These pixels 444*f*, 446*f* and 448*f* are used to define an interpolation spline 605 in the image frame shown in FIG. 6. The camera 350 may also be used to capture an exemplary image of an exemplary area of skin having a certain morphology marked by a plurality of projected fiducials. For example, the fiducials may be captured at pixels 611, 612, 613 and 614 of the image frame shown in FIG. 6.

Figure 7:
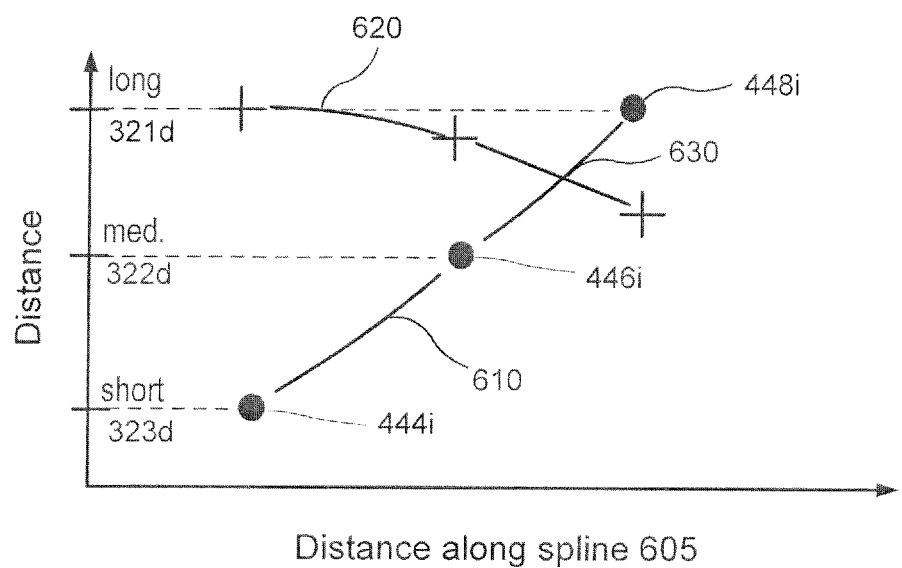
FIG. 7 shows a graphical representation of the application calibration data and a curve corresponding to the morphology of the exemplary area of skin determined using projected fiducials for the exemplary image frame of FIG. 6.

As shown in FIG. 7, a morphology of the skin as determined by a plurality of fiducials (e.g., comparing fiducials captured in an image of the skin at pixels 611, 612, 613 and 614 to an exemplary set of fiducial calibration data) may be compared to applicator calibration data to identify a region within an image of the skin captured by the camera 350 that corresponds to an aimed location of the applicator 340. In FIG. 7, each pixel along the interpolation spline 605 of the image frame is mapped to a distance between the probe and a height of the corresponding location on this skin, determined using image data corresponding to the exemplary image and the exemplary set of fiducial calibration data, as shown in spline 620. The applicator calibration data may also be interpolated to correlate each pixel 444*f*, 446*f*, 448*f* along interpolation spline 605 with a distance (e.g., distance measurements 321*d*, 322*d*, 323*d* corresponding to the short distance 321, the medium distance 322, and the long distance 323 shown in FIG. 2) between the probe 310 and the substrate, which is represented by data points 444*i*, 446*i* and 448*i* in FIG. 7, respectively. The distances corresponding to interpolation spline 605 are shown along spline 610 in FIG. 7. As can be seen in FIG. 7, splines 610 and 620 intersect at position 630, which represents the pixel along spline 505 in the image frame of FIG. 6 corresponding to the aimed location of applicator 340 for the exemplary area of skin having a morphology as determined by the projected fiducials captured at pixels 611, 612, 613 and 614 of the image frame shown in FIG. 6.

Example IV

Example IV provides an exemplary embodiment of an optical emitter 110 projecting a plurality of fiducials in a checkerboard pattern. In particular, the optical emitter 110 may comprise a fiducial light source, preferably, a non-laser light source, and a gobo having a checkerboard pattern with multiple alternating squares, through which light from the fiducial light source would pass to project checkerboard patterned fiducials to the skin. This gobo having a checkerboard pattern is particularly useful with a LED fiducial light source, which is believed to be safer than a laser fiducial light source for use on or near the eyes of a person. The gobo may be screened onto a protective window that is parallel or substantially parallel to an average orientation of skin such that the fiducials projected through the gobo onto the skin are free or substantially free of keystone distortion. In this embodiment, the checkerboard patterned fiducials are a particularly efficient way to utilize a single fiducial light source to project a plurality of fiducials points on the skin. Alternatively, the optical emitter 110 may comprise a laser fiducial light source that is projected through a phased holographic plate having a plurality of different surface features for diffracting and/or phase varying the laser light source to project a checkerboard pattern. The combination of a laser fiducial light source through a phased holographic plate provides focused and/or sharp optical fiducials and may be used for projecting a plurality of fiducials in a checkerboard pattern onto treatment surfaces, particularly, skin away from the eyes of a person where projected laser fiducials do not present an increased safety risk as compared to non-laser optical fiducials.

Figure 8A:
FIG. 8a shows an exemplary control image of a skin of a hand without any projected optical fiducials.
Figure 8B:
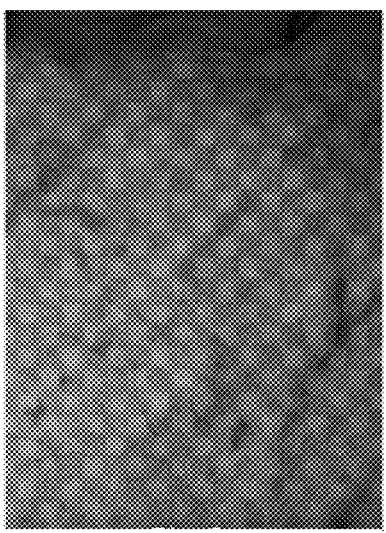
FIG. 8b shows an exemplary image of the same area of skin of FIG. 8a, where checkerboard patterned fiducials are projected to the skin in both green light and red light, the image simulated as being captured by a sensor in a green channel.
Figure 8C:
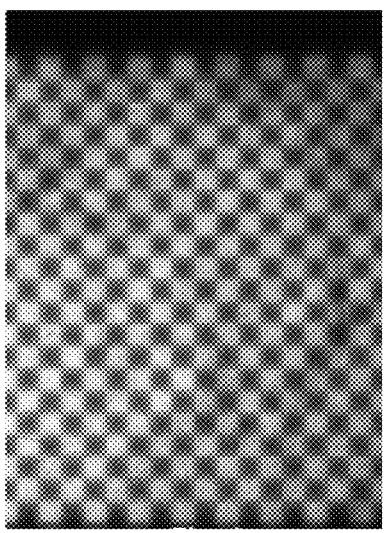
FIG. 8c shows an exemplary image of the same area of skin and having the same projected checkerboard patterned fiducials in both green light and red light as FIG. 8b, the image simulated as being captured by a sensor in a red channel.
Figure 8D:
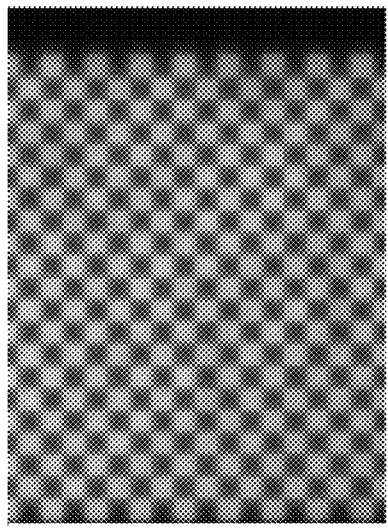
FIG. 8d shows an exemplary image of the same area of skin having the same projected checkerboard patterned fiducials in both green light and red light as FIG. 8c, the image simulated as an image captured in a red channel normed by data corresponding to image captured in a green channel to reduce distortions to the checkerboard patterned fiducials caused by variations in the color and texture of the skin.
Figure 8E:
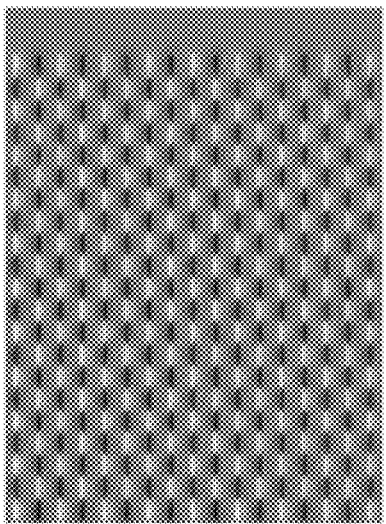
FIG. 8e shows an exemplary processed image generated by small vertical averaging and horizontal differentiation of the image of FIG. 8d to show vertical edges of the checkerboard patterned fiducials.
Figure 8F:
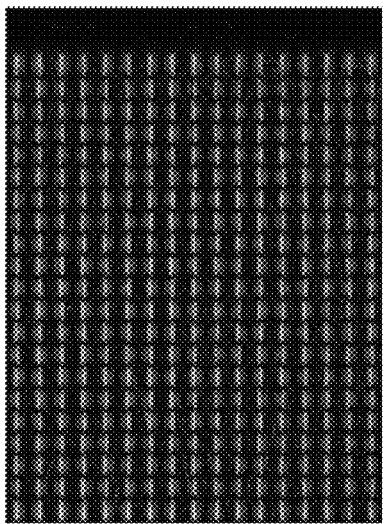
FIG. 8f shows an exemplary processed image generated as an absolute value of the image of FIG. 8e.
Figure 8G:
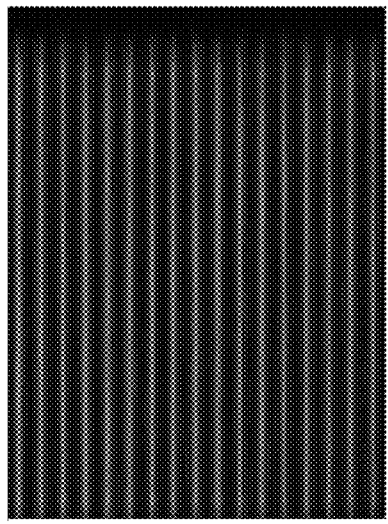
FIG. 8g shows an exemplary processed image generated by processing the image of FIG. 8f to average edges of the checkerboard pattern vertically along exactly two squares.
Figure 8H:
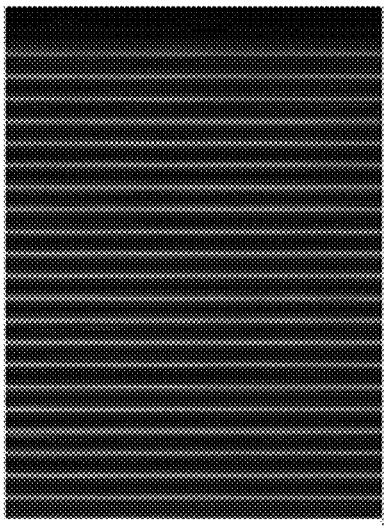
FIG. 8h shows an exemplary processed image processed in a similar manner as the image of FIG. 8g, except in a horizontal direction.
Figure 8I:
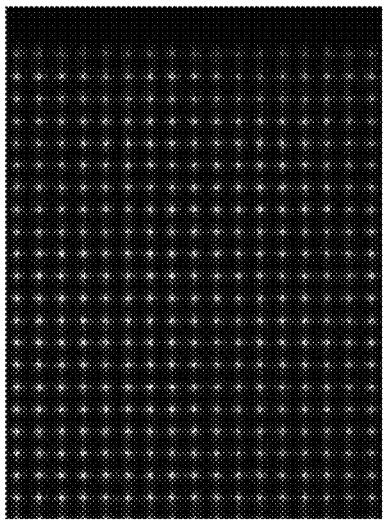
FIG. 8i shows an exemplary processed image that is obtained by multiplying the image of FIG. 8g with the FIG. 8h to reveal fiducial points at corners of the checkerboard pattern.

In addition, the checkerboard patterned fiducials, as described above, can provide distinguishable spatial events at the corners of each of the squares of the checkerboard pattern that can act as individually identifiable fiducials points on the skin, an example of which is shown in FIG. 8i. These spatial events at the corners of each of the squares of the checkerboard patterned fiducials can provide sharp distinguishable fiducial points without use of a laser fiducial light source.

Fiducials projected in a checkerboard pattern may be particularly beneficial for numerous reasons. First, a gobo having a checkerboard pattern allows half of the light from the fiducial light source to pass through, and therefore, provides a pattern that efficiently utilizes light emitted from the fiducial light source. In contrast, a gobo having a pattern for projecting an array of pinholes allows a smaller portion of light emitted from the fiducial light source to pass therethrough and therefore, much of the light emitted from the fiducial light source is wasted and not utilized with a pinhole patterned gobo. Second, fiducials projected in a checkerboard pattern provides marks that can be detected not as points but along line edges, which may improve precision and/or accuracy of positions mapped using the checkerboard pattern fiducials. The checkerboard pattern fiducials may provide marks that are detectable along line edges and can be used for positional determination based on an average of the points across the line, which reduces the amount of distortion that may be caused by variation in the color or texture of the skin. The checkerboard pattern also includes edges that alternate in polarity, and thereby on average negates possible edge bias of the fiducials. Third, the checkerboard pattern may be in an N by N pattern providing fiducials having 2N lines, instead of $N^2$ single point fiducials, which may reduce the likelihood of misclassification of single point fiducials.

FIG. 8a shows a control image of an area of skin on a hand obtained through a circular polarizer and doubled in contrast. FIGS. 8b through 8i show various simulated images for the same area of skin from FIG. 8a where a checkerboard pattern is projected to the skin in a green light and also overlaid with the same checkerboard pattern in a red light. The checkerboard patterned fiducials are processed in different manners are shown in FIGS. 8b to 8i to demonstrate the checkerboard pattern fiducials under different conditions.

As discussed above, the image data from the detector arrangement 120 may be further adjusted, manipulated or processed under various conditions so as to sharpen the fiducials within the processed image data and/or to remove interfering background noise from the image data before the processed image data is analyzed to determine a morphology of the area of skin. In particular, in an image that is marked by checkerboard patterned fiducials, the image data may be further manipulated and/or processed to sharpen fiducial points at each of the corners of the squares of the checkerboard patterned fiducials to provided improved precision for identification of the locations of these fiducial points in the image. For example, image data corresponding to an image of an area of the skin marked with fiducials, may be normed using a secondary set of image data corresponding to an image of the area captured without fiducial markings. In some embodiments, the secondary set of image data may be obtained under a different lighting condition. In one example, the image data may be obtained using one color channel and the secondary set of image data may be obtained using a different color channel. The second set of image data may correspond to an entire image or to certain components of the image, such as, for example, gamma luminance of the image. The image data may be normed by the secondary set of image data by pixel division of the image data divided by the secondary set of image data to generate a new set of processed image data. It is noted that this further adjustment to the image data (e.g., normed using the secondary set of image data) may be applied to image data corresponding to an image marked by checkerboard patterned fiducials formed from any suitable fiducial light source, including LED and/or laser.

Figure 9A:
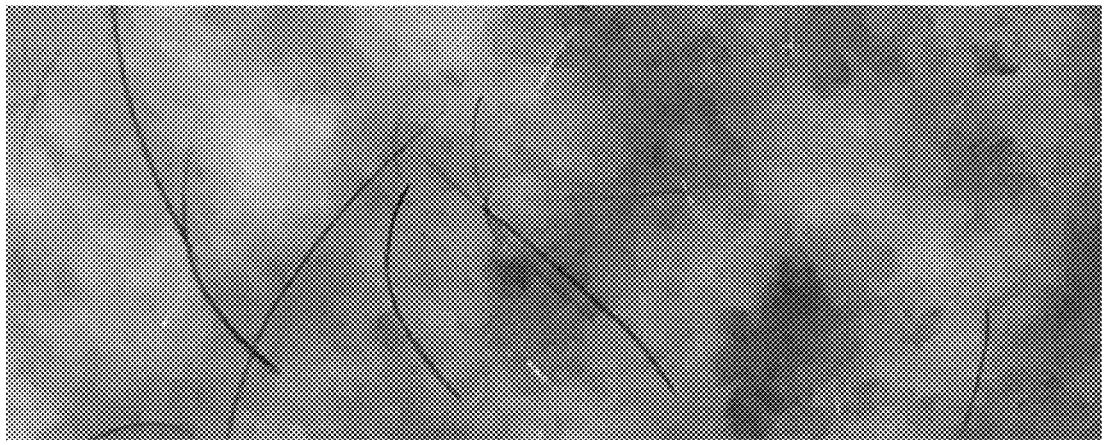
FIG. 9a shows an in-depth view of the exemplary processed image of FIG. 8c having an increased magnification.
Figure 9B:
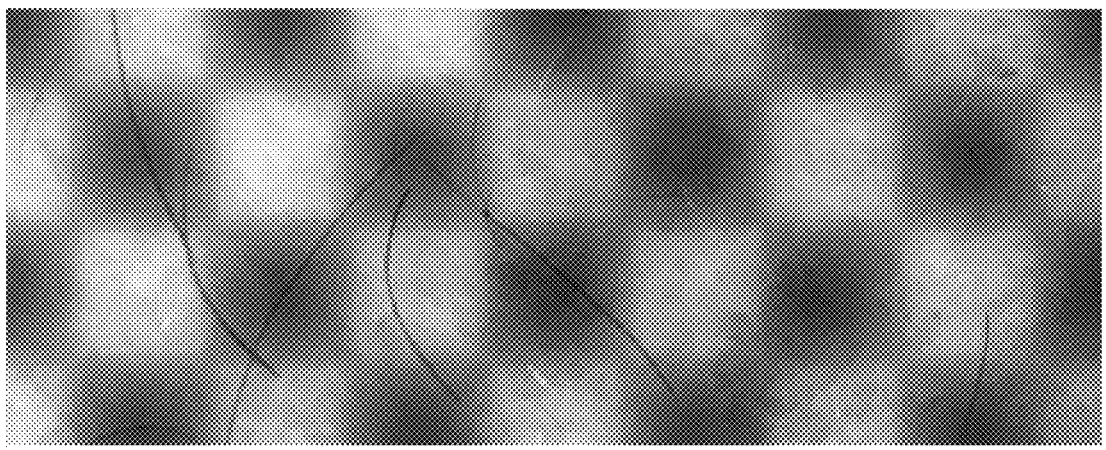
FIG. 9b shows an in-depth view of the exemplary processed image of FIG. 8d having an increased magnification.
Figure 9C:
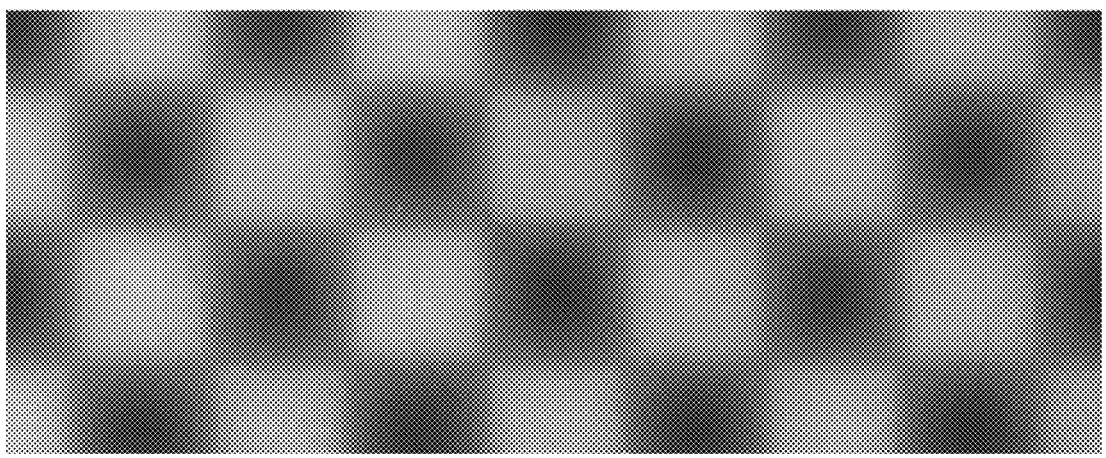
FIG. 9c shows an in-depth view of the exemplary processed image of FIG. 8e having an increased magnification.

In the exemplary embodiment shown in FIG. 8d, the exemplary image data of FIG. 8c, which is an image of a skin captured by a sensor in a red channel, is normed by data corresponding to an image of the skin captured in a green channel so as to reduce distortions to the checkerboard patterned fiducials caused by variations in the color and texture of the skin. The distortions may be caused by unevenness in color or texture of the skin. In particular, the skin may be uneven in color and include various dark regions that possess higher concentrations of melanin that can cause distortions to the projected fiducials (e.g., broadening and/or blurring of the fiducials) as light diffuses away from the dark region. The distortions contribute to errors in identifying the correct positioning of the fiducials captured in an image of a region of skin having dark regions. By norming the image data with a secondary set of image data obtained using a different color channel, distortions to the fiducials caused by variations in the color and texture of the skin can be reduced. More particularly, the imaged data may be normed with a bias towards the red channel, such as, for example, by a biasing power from about 0.6 to about 1.0 of the green channel, because skin variations tend to be more visually apparent under green light than in red light. In an alternative embodiment, the fiducials may be projected in a blue light and the biasing power towards the red channel may be about 1.0. The exemplary image shown in FIG. 8d is normed using a biasing power of 0.6 of the green channel. FIGS. 9a-c show more in-depth views of the images of FIGS. 8c-e, respectively, at an increased magnification. As can be seen in these exemplary images, the normed image of FIGS. 8d and 9b show a sharper image, in particular, a clearer image of the edges of the checkerboard patterned fiducials. Although the forming process is described above using checkerboard patterned fiducials, it is contemplated that the norming process may be utilized with any type of projected fiducials to reduce distortions to the fiducials caused by variations in the color and texture of the skin.

Image data corresponding to an image of skin including the checkerboard patterned fiducials may be normed as discussed above and further processed to identify individual fiducial points corresponding to the corners of each of the squares of the checkerboard pattern. Vertical components of the checkerboard patterned fiducials may be isolated from an image, such as, for example, in the image shown in FIG. 8g. Similarly, horizontal components of the checkerboard patterned fiducials may be obtained from an image, such as, for example, in the image shown in FIG. 8h. The intersections of these vertical and horizontal components reveal individual fiducial points corresponding to the corners of each of the squares of the checkerboard pattern, as can be seen in FIG. 8i. The fiducial points at the corners of each of the squares of the checkerboard patterned fiducials can each be used as a separate fiducial mark for identifying the morphology of an area of skin as discussed above.

Although Examples I-IV are described herein with reference to alignment of a cosmetic spray from a cosmetic applicator, any other topical spray (e.g., a skin treatment composition for improving the appearance and/or health of the skin) from a topical composition applicator can also be aligned similarly as described above in these examples.

The invention described and claimed herein is not to be limited in scope by the specific embodiments herein disclosed since these embodiments are intended as illustrations of several aspects of this invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. All publications cited herein are incorporated by reference in their entirety.

What is claimed is:

1. A method for application of a composition to a treatment surface of a user, comprising:
    projecting, by an optical emitter, a plurality of fiducials to the treatment surface, wherein the plurality of fiducials form a pattern;
    obtaining, by a detector arrangement, image data corresponding to an image of an area of the treatment surface marked with the fiducials;
    analyzing, by a processing arrangement, the image data to determine a morphology of the area of the treatment surface based on the fiducials captured within the image, wherein the morphology of the area of the treatment surface is determined using the fiducial points corresponding to corners of the pattern;
    identifying, by the processing arrangement, a region within the image aligning to a location within the area of the treatment surface aimed for application of the composition by an applicator arrangement, the region aligning to the aimed location of the applicator arrangement is identified based on the morphology of the area of the treatment surface;
    analyzing, by the processing arrangement, the image data to determine whether the identified region within the image corresponds to an artifact; and
    selectively applying, by an applicator arrangement, the composition to the location within the area of the treatment surface when the artifact is detected from the identified region, wherein the applicator arrangement comprises a nozzle configured to deposit the composition from a pressurized reservoir to form a thin layer of the composition on the treatment surface.

2. The method of claim 1, wherein the treatment surface is a skin of a face of the user.

3. The method of claim 1, wherein at least 3 fiducials are projected to the treatment surface.

4. The method of claim 1, wherein the plurality of fiducials forms a checkerboard pattern.

5. The method of claim 4, wherein the morphology of the area of the treatment surface is determined using the plurality of fiducial points corresponding to corners of the checkerboard pattern.

6. The method of claim 1, wherein the morphology is determined by analyzing the image data to determine, for each fiducial, a distance between the optical emitter and a height of a position on the treatment surface marked by each fiducial.

7. The method of claim 6, wherein the distance is determined by analyzing the image data to compare a fiducial position of each fiducial within the image to calibration data, the calibration data correlating regions within calibration images of a calibration substrate captured by the detector arrangement to distances between the optical emitter and the calibration substrate.

8. The method of claim 6, wherein the morphology comprises at least one of a curvature and a tilt of the area of the treatment surface.

9. The method of claim 1, wherein the processing arrangement determines whether the identified region corresponds to the artifact based on a reflectance of the treatment surface detected in the image.

10. The method of claim 1, wherein the composition is a cosmetic composition comprising a reflectance modifying agent.

11. The method of claim 1, wherein the composition comprises an active ingredient for treating a skin condition.

12. The method of claim 1, wherein the analyzing step comprises adjusting the image data to reduce distortions to the fiducials captured within the image, and determining the morphology of the area of the treatment surface based on the fiducials captured within the image using the processed image data.

13. The method of claim 12, wherein the image data is adjusted using a second set of image data corresponding to at least one component of a second image of the area of the treatment surface obtained by the detector arrangement, wherein the second image is not marked with the fiducials.

14. A handheld device for applying a composition to a treatment surface, comprising:
    an optical emitter configured to project a plurality of fiducials to the treatment surface, wherein the plurality of fiducials form a pattern;
    a detector arrangement configured to obtain image data corresponding to an image of an area of the treatment surface marked with the fiducials;
    an applicator arrangement configured to apply the composition to a location within the area of the treatment surface, wherein the applicator arrangement comprises a nozzle configured to deposit the composition from a pressurized reservoir to form a thin layer of the composition on the treatment surface; and
    a processing arrangement configured to receive the image data from the detector arrangement, analyze the image data to determine a morphology of the area of the treatment surface based on the fiducials captured within the image, identify a region within the image aligning to the location the applicator arrangement is configured to apply the composition, the region aligning to the aimed location of the applicator arrangement is identified based on the morphology of the area of the treatment surface, wherein the morphology of the area of the treatment surface is determined using the fiducial points corresponding to corners of the pattern, analyze the image data to determine whether the identified region corresponds to an artifact, and direct the applicator arrangement to selectively apply the composition to the location when the artifact is detected from the identified region.

15. The handheld device of claim 14, wherein the plurality of fiducials comprises at least 3 fiducials.

16. The handheld device of claim 14, wherein the at least one optical emitter comprises a fiducial light source and a template through which light from the fiducial light source would pass to project the plurality of fiducials to the area of the treatment surface.

17. The handheld device of claim 14, wherein the plurality of fiducials forms a checkerboard pattern.

18. The handheld device of claim 14, wherein the detector arrangement comprises at least one light source for delivering light to the area of the treatment surface, and at least one sensor for detecting the light and the projected fiducials from the area of the treatment surface to obtain the image data.

19. The handheld device of claim 14, wherein the applicator arrangement comprises a nozzle configured to deposit the composition from a pressurized reservoir to form a thin layer of the composition on the treatment surface.

20. The handheld device of claim 14, wherein the composition comprises at least one of a reflectance modifying agent and an active ingredient for treating a skin condition.

21. The handheld device of claim 14, wherein the processing arrangement determines the morphology by analyzing the image data to determine, for each fiducial, a distance between the optical emitter and a height of a position on the treatment surface marked by each fiducial.

22. The handheld device of claim 21, further comprising a non-transitory computer-accessible medium configured to store calibration data, the calibration data correlating regions within calibration images of a calibration substrate captured by the detector arrangement to distances between the optical emitter and the calibration substrate, and wherein the processing arrangement determines the distance between the optical emitter and the height of the position on the treatment surface marked by each fiducial by comparing a fiducial position of each fiducial within the image to the calibration data.

23. The handheld device of claim 14, wherein the morphology comprises at least one of a curvature and a tilt of the area of the treatment surface.

24. The handheld device of claim 14, wherein the processing arrangement determines whether the region within the image includes the artifact based on a reflectance of the treatment surface detected in the image.

* * * * *